(12) United States Patent
Knipple, Jr. et al.

(10) Patent No.: US 7,811,278 B2
(45) Date of Patent: Oct. 12, 2010

(54) FLUID CONNECTOR

(75) Inventors: Larry Eugene Knipple, Jr., Wellington, CO (US); Mark Allen Stone, Loveland, CO (US); David Warren Splett, Fort Collins, CO (US)

(73) Assignee: Cuffco, LLC, Saint Augustine, FL (US)

( * ) Notice: Subject to any disclaimer, the term of this patent is extended or adjusted under 35 U.S.C. 154(b) by 0 days.

(21) Appl. No.: 11/673,591

(22) Filed: Feb. 11, 2007

(65) Prior Publication Data

US 2008/0191466 A1 Aug. 14, 2008

(51) Int. Cl.
A61M 25/16 (2006.01)

(52) U.S. Cl. .................. 604/535; 604/533; 604/534

(58) Field of Classification Search .............. 604/533, 604/534, 535, 536, 537, 538, 539; 285/921
See application file for complete search history.

(56) References Cited

U.S. PATENT DOCUMENTS

| 3,667,785 A * | 6/1972 | Kapeker ............... 285/231 |
| 4,022,205 A | 5/1977 | Tenczar |
| 4,030,494 A | 6/1977 | Tenczar |
| 4,030,850 A * | 6/1977 | Hyde ................ 403/288 |
| 4,335,753 A | 6/1982 | Frye |
| 4,591,192 A | 5/1986 | Van Exel et al. |
| 4,676,530 A | 6/1987 | Nordgren et al. |
| 4,844,512 A * | 7/1989 | Gahwiler ............. 285/39 |
| 4,875,719 A | 10/1989 | Mylett |
| 4,949,745 A | 8/1990 | McKeon |
| 5,536,049 A | 7/1996 | Coules et al. |
| 5,549,583 A * | 8/1996 | Sanford et al. ............ 604/535 |
| 5,685,866 A | 11/1997 | Lopez |
| 5,797,633 A | 8/1998 | Katzer et al. |
| 5,868,440 A | 2/1999 | Kurz |
| 6,086,574 A * | 7/2000 | Carroll et al. ............ 604/533 |
| 6,543,814 B2 | 4/2003 | Bartholomew |
| 6,893,055 B2 | 5/2005 | Thomas et al. |
| 7,014,224 B1 | 3/2006 | Sward |
| 2004/0164547 A1 | 8/2004 | Cronley |
| 2005/0211934 A1 | 9/2005 | Garber et al. |
| 2006/0049634 A1 | 3/2006 | Goodsel et al. |

FOREIGN PATENT DOCUMENTS

GB 1193759 6/1970

* cited by examiner

*Primary Examiner*—Kevin C. Sirmons
*Assistant Examiner*—Laura C Schell
(74) *Attorney, Agent, or Firm*—Roger A. Jackson

(57) ABSTRACT

A fluid connector and method of use is disclosed that includes a male housing with a male proximal end portion adapted to be in fluid communication with a first line and a male distal end portion having a resilient ring. Also included is a female housing with a female proximal end portion adapted to be in fluid communication with a second line and a female distal end portion with a resilient annulus that removably engages the ring. Operationally, the male and the female housings are configured at the annulus and ring engagement to have a high separating resistance axially and a low separating resistance transverse to the axial axis by manually applying a bending moment between the male and female engaged housings by a force transverse to the axial axis. Further included is structure for fluid sealing between the male and female housings when the annulus and ring are engaged.

15 Claims, 32 Drawing Sheets

FLUID CONNECTOR

TECHNICAL FIELD

The present invention generally relates to a fluid connector and more particularly to a removably engagable fluid connector that includes a sealing element for maintaining a substantially fluid tight connection for the purpose of facilitating fluid communication between a plurality of fluid lines.

BACKGROUND OF INVENTION

There are a variety of fluid connectors in the prior art. The majority of disclosed prior art fluid connectors are designed for quick (tool less) couple and release of a fluid line, usually by the use of latches or flexible fingers which involve additional moving parts and complication. There are many issues surrounding the fluid connector such as, how to handle the many different types of fluids and their properties, such as viscosity, miscibility of the various fluid components, also fluid pressure capability, fluid sealing capabilities at the connector interface, ease of assembly and disassembly, and fluid line interface particulars.

In addressing the above-identified issues that are common to fluid connectors, the prior art discloses a number of different types of connectors. Looking to a typical tool-less fluid connector that includes fluid sealing capabilities, in United Kingdom patent number GB1,193,159 to Sarns disclosed is a molded plastic coupling used with flexible tubing for medical appliances. In Sarns the pinching of the outside diameter of the connector releases the interlock on "L" shaped fingers, wherein a telescoping connection uses male gland o-rings for fluid sealing with the Sarns connector typically being applied to a medical intravenous tube feed fluid communication line for a patient. Another example is in U.S. Pat. No. 6,893,055 to Thomas et al. that discloses a tubing snap connector that utilizes an outside diameter resilient sleeve that acts as a ring retainer also having a male gland o-ring for fluid sealing between the tubing ends. Thomas et al. requires that the sleeve have a spring arm and stop cam combination that radially encompasses a portion of sleeve circumference, thus facilitating assembly without the need for multiple pieces to secure around the tubing outside ridge, however, still having a separable piece. Similarly, in U.S. Pat. No. 4,591,192 to Van Exel et al. disclosed a quick connect coupling for a garden hose that uses line pressure to add friction to the clip that is received into a groove in the male nozzle, thus making the coupling less prone to separating inadvertently under pressure. Van Exel et al., like Thomas et al. still requires separable pieces for the fluid connector to make a removable engagement. Further, being somewhat similar to Sarns, in U.S. Pat. No. 6,543,814 to Bartholomew disclosed is a quick connector for tubing without the need for tools that is fluid tight and allows for swiveling. Bartholomew uses deflectable fingers that are received into a mating annular bead, wherein a locking tab that engages the annular channel to lock the connector, however, again resulting is a complex assembly of parts. Further, in this area in United States patent application publication number US2004/0164547 A1 to Cronley, disclosed is a quick connect coupler for hoses and pipes that uses a plurality of partial threaded segments in the form of flexible fingers. In Cronley, the threaded segments form a flexible collet for non turning required threaded engagement, having again a multitude of parts being required.

Another type of fluid connector is what is called a "luer type" again for use in medical and surgical applications, wherein the luer has a frustroconical shaped outer surface having a fluid passage within the interior of the frustroconical section. Typically a luer type fitting matably engages a male frustroconical outer surface section with a female frustroconical inner surface section in attempting to achieve a substantially fluid removable interface. However, this aforementioned luer type engagement requires ancillary means for axial retention of the luer interface (interspaced between the tubing ends), wherein the luer interface itself has little axial retention other than the surface friction between the male and female frustroconical sections, unfortunately both the taper nature of the luer engagement and any pressure within the fluid line all act to forcibly separate the luer interface axially, resulting in an unacceptable situation for loss of fluid communication between the tubing ends. An example of a means for axial retention of a luer type fitting is in U.S. Pat. No. 4,676,530 to Nordgren et al. that discloses a coupling device for connecting fluid flow conduits to each other with a male luer lock fitting to insure against axial separation. Nordgren et al. uses an inwardly flexibly fingered collet that radially grips the outer tapered section of the male frustroconical section for a easily insertable interface of the frustroconical section by the increasing diameter frustroconical surface moving through the collet fingers, however, Nordgren et al. does not have an easily removable connection as either the fingers and/or male frustroconical outer surface would be damaged. Thus the Nordgren et al. connector is basically a one time use disposable connector.

Further, in this same area of luer type fittings in U.S. Pat. No. 7,014,224 to Sward disclosed is a refinement to the luer type connector for enhanced fluid sealing that includes a fluid line connector for connecting two fluid lines by coupling a male and female portion together with a slip ring to lock the male and female couplers. Sward utilizes the mating of o-ring scalable frustroconical portions that are engaged by a slip ring that is locked by a leaf spring, while being functional at being a fluid sealed connector, does posses a number of parts that add to complexity.

Other special purpose type fluid connectors are disclosed in the prior art such as in U.S. Pat. No. 4,949,745 to McKeon that discloses a connector using two couplers held between a pair of o-rings to produce a fluid path that can be assembled in a contaminated environment without contaminating the fluid, in other word due to internal valving and chambering the fluid within the lines is not exposed to the outside environment, i.e. not being released from the fluid line until the connector is secured together. McKeon utilises a multitude of sealed chambers that prevent exposure of the fluid within the connector to the external environment during the connecting and disconnecting of the couplers, however, resulting in a highly complex fluid connector. Being similar functionally, in U.S. Pat. No. 4,030,494 to Tenczar disclosed is a fluid connector that is sealed by a resilient barrier of a flexible diaphragm type structure until assembled with another mating connector where in the resilient barrier is penetratable during assembly by the use of heat to fuse and sterilize the penetrated barrier, thus accomplishing what McKeon does, however, again with Tenczar being a one-time use and thus disposable.

A further specialized type of fluid connector is in U.S. Pat. No. 5,685,866 to Lopes that discloses a medical use valve that reseals after use i.e. for the adding of fluid medicine to a patients intravenous line without the risk of plug coring (from the syringe) contaminants entering into the patient through the intravenous fluid line. The point in Lopez is the ability to enter into a pressurized fluid line by inserting a syringe into a resilient medium that will seal around the syringe, while the syringe is passed through the resilient medium and into the open interior of the fluid line without the syringe cutting or dislodging any of the resilient medium into the fluid by use of a blunt nose syringe with a side discharge port. Another type of fluid tube connector for adjoining to a fixed port is in U.S. Pat. No. 5,536,049 to Coules et al. that discloses a flexible tube connector that is an outside diameter compression ferrule type that has a positive stop that limits engagement of the retaining member and the tube. The purpose in Coules et al., is in a positive stop that prevents damage to the tube by acting as a gage in limiting compression of the flexible tube, however, still resulting in a fairly complex assembly. Somewhat similar to Coules et al., in U.S. Pat. No. 5,868,440 to Kurz disclosed is a hose connector specifically for soft wall hoses for the purpose of minimizing cutting, leaking, and slipping of the hose to connector interface. Kurz utilizes a toroidal spring that is compressed in a frustroconical chamber against the hose to provide a sufficient wide area loading that is adequate for fluid sealing between the hose and the connector. Like Kurz, in U.S. Pat. No. 5,797,633 to Katzer et al. disclosed is a hose connector that uses pivotal gripping elements as against a frustroconical surface to compress the hose into the connector. Katzer et al. has the gripping elements in conjunction with the two part sleeve to control hose compression to prevent hose damage, however, again resulting in a multitude of complex parts.

In looking at simplified fluid connectors, in U.S. Pat. No. 4,215,119 to Mylett disclosed is a universal hose connector that has a frustroconical portion that has a series of circular barb rings to accommodate numerous sizes of hose diameters. Mylett has "sets" of increasing size circular barb rings that increases the bite of the barb ring into the tubing for retention purposes, however, a drawback of Mylett being that multiple engaging and disengaging would be difficult as the tubing would not easily disengage from the multiple barbs sets which would also have a tendency to damage the tubing due to their "shark teeth" type of profile.

What is needed is a simplified fluid connector without moving or separable parts that can accomplish a multiple use removable engagement of a fluid connection without replacing parts, can also have a substantially fluid tight sealed connection while at the same time minimizing the parts required for simplicity and reliability. In addition the fluid connector should have a firm engagement when manually assembled, while also being easy to manually disengage, without the need for tools in any case.

SUMMARY OF INVENTION

The present invention is a fluid connector for facilitating fluid communication between a first line and a second line that includes a male housing with a male proximal end portion adapted to be in fluid communication with the first line and a male distal end portion having an especially deformable ring. Wherein, a male longitudinal axis spans between the male housing proximal end portion and the male housing distal end portion. Also included in the fluid connector is a female housing including a female proximal end portion adapted to be in fluid communication with the second line and a female distal end portion with an elastically deformable annulus that removably engages the ring. Wherein, a female longitudinal axis spans between the female housing proximal end portion and the female housing distal end portion. Operationally the male housing and the female housing are sized and configured at the annulus and ring engagement to have a high separating resistance coaxially substantially along said male and female longitudinal axes and a low separating resistance substantially transverse to the male and female longitudinal axes by manually applying a bending moment between the male and female engaged housings by application of a manual force substantially transverse to the male and female longitudinal axes. Further included in the fluid connector is structure for substantially fluid sealing between the male housing and the female housing when the annulus and ring are engaged.

These and other objects of the present invention will become more readily appreciated and understood from a consideration of the following detailed description of the exemplary embodiments of the present invention when taken together with the accompanying drawings, in which;

REFERENCE NUMBERS IN DRAWINGS

Figure 1:
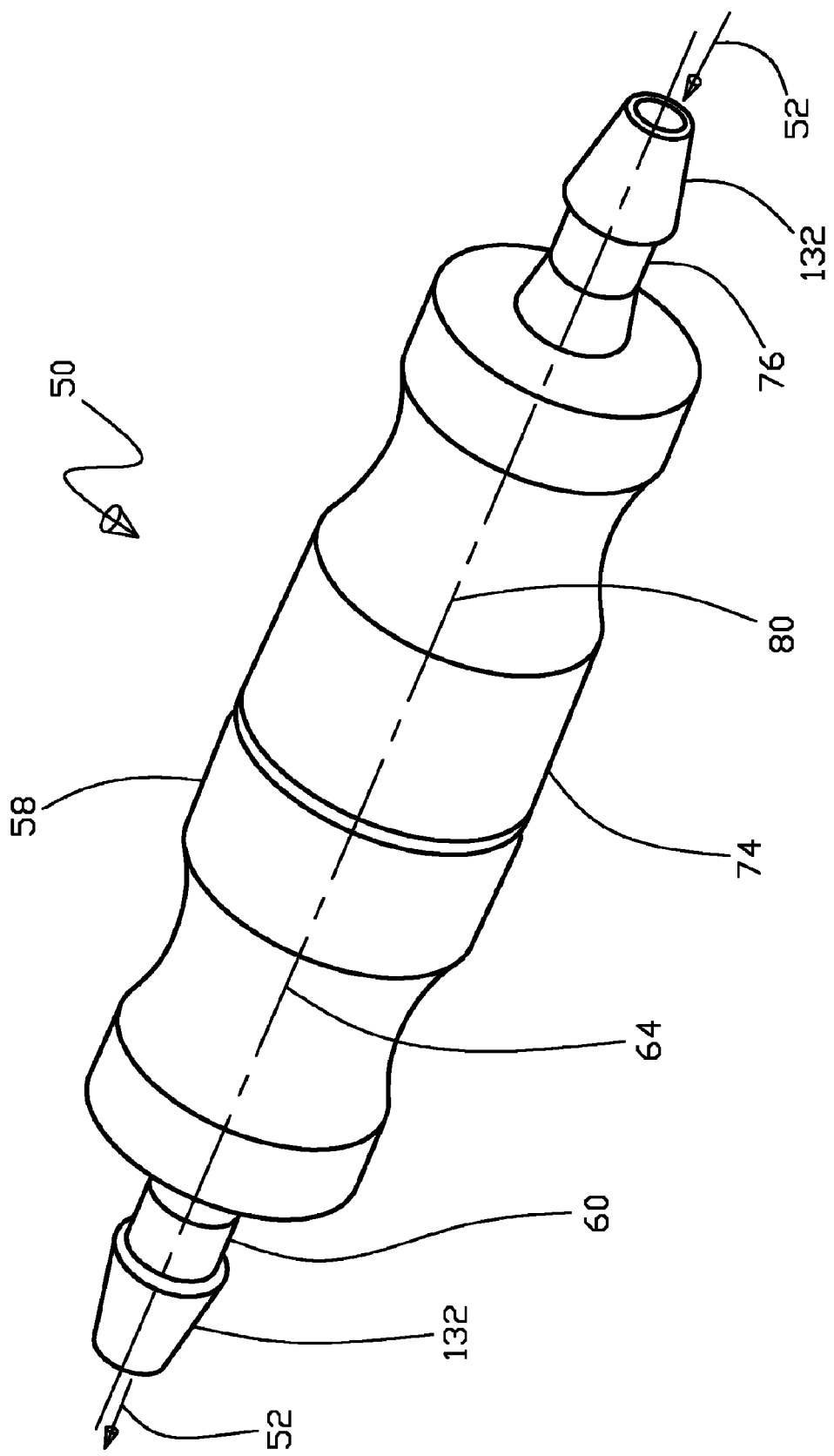
FIG. 1 is a perspective view of the fluid connector with the male housing and female housing removably engaged to one another, shown as being adapted for the barbed fluid line interface.

50 Fluid connector
52 Fluid communication
54 First fluid line
56 Second fluid line
58 Male housing
60 Proximal end portion of male housing 58
62 Distal end portion of male housing 58
64 Longitudinal axis of male housing 58
65 Surrounding side wall of male housing 58
66 Elastically deformable ring
68 Outside diameter of deformable ring 66
70 Adjacent gradual radius of deformable ring 66
72 Adjacent sharp radius of deformable ring 66
74 Female housing
76 Proximal end portion of female housing 74
78 Distal end portion of female housing 74
80 Longitudinal axis of female housing 74
81 Surrounding side wall of female housing 74
82 Elastically deformable annulus
84 Removable engagement of annulus 82 and ring 66
86 Ring 66 disposed within annulus 82
88 Inner ridge of annulus 82
90 Interfere nee fit bet we en annulus 82 and ring 66
92 Annulus profile to substantially match the ring's 66 profile of a gradual radius 70, a ring outside diameter 68, and a sharp radius 72
94 Clearance radial fit between the annulus 82 and the ring 66
96 Interference axial fit between the annulus 82 and the ring 66
98 Substantially tight axial fit between the male housing 58 and the female housing 74
100 High substantially coaxial separating resistance of annulus 82 and ring 66 engagement 84
102 Low axial force along the male 64 and female 80 longitudinal axes to engage 84 the annulus 82 and the ring 66
104 High axial force or engagement force along the male 64 and female 80 longitudinal axes wherein a high axial opposing force 100 is required to disengage 84 the annulus 82 and the ring 66
106 Low separating resistance direction substantially transverse to the male 64 and female 80 longitudinal axes 108 Manually applying a bending moment between the male 58 and female 74 engaged 84 housings
110 Manual force substantially transverse to the male 64 and female 80 longitudinal axes
111 Human user of fluid connector 50 in medical application
112 Human hand
113 Provider of fluid in medical application
114 Manually engaging and manually disengaging the fluid communication 52 between the first line 54 and the second line 56
116 Male 58 and female 74 housings sized and configured to be manually grasped by a human hand 112
118 Attaching the male proximal end portion 60 to the first line 54
120 Attaching the female proximal end portion 76 to the second line 56
122 Positioning the male housing longitudinal axis 64 and the female housing longitudinal axis 80 to be substantially co-axial with one another and the male housing distal end 62 and the female housing distal end 78 to face one another
124 Pushing the male housing distal end 62 and female housing distal end 78 together
126 Operationally causing disengagement of the annulus 82 and ring 66 and therefore disengagement 84 of the male 58 and female 74 housings
132 Barbs of the proximal end portions 60 and 76 of both the male 58 and female 74 housings
134 Threads of the proximal end portions 60 and 76 of both the male 58 and female 74 housings
136 Luer taper of the proximal end portions 60 and 76 of both the male 58 and female 74 housings
135 Means for substantial fluid sealing between the male housing 58 and the female housing 74
140 Face seal
141 Face seal 140 channel
142 Face seal 140 o-ring
144 Male gland seal
146 Male gland 144 o-ring
147 Male gland seal 144 channel
148 Female gland seal
150 Female gland 148 o-ring
151 Female gland seal 148 channel
152 O-ring positioned adjacent to the annulus 82 and the ring 66
154 Selective axial compression of the face seal 140 o-ring 142
156 Selective fit between the annulus 82 and the ring 66 acting as an axial gage for the selected axial face seal 140 o-ring 142 compression

DETAILED DESCRIPTION

Figure 2:
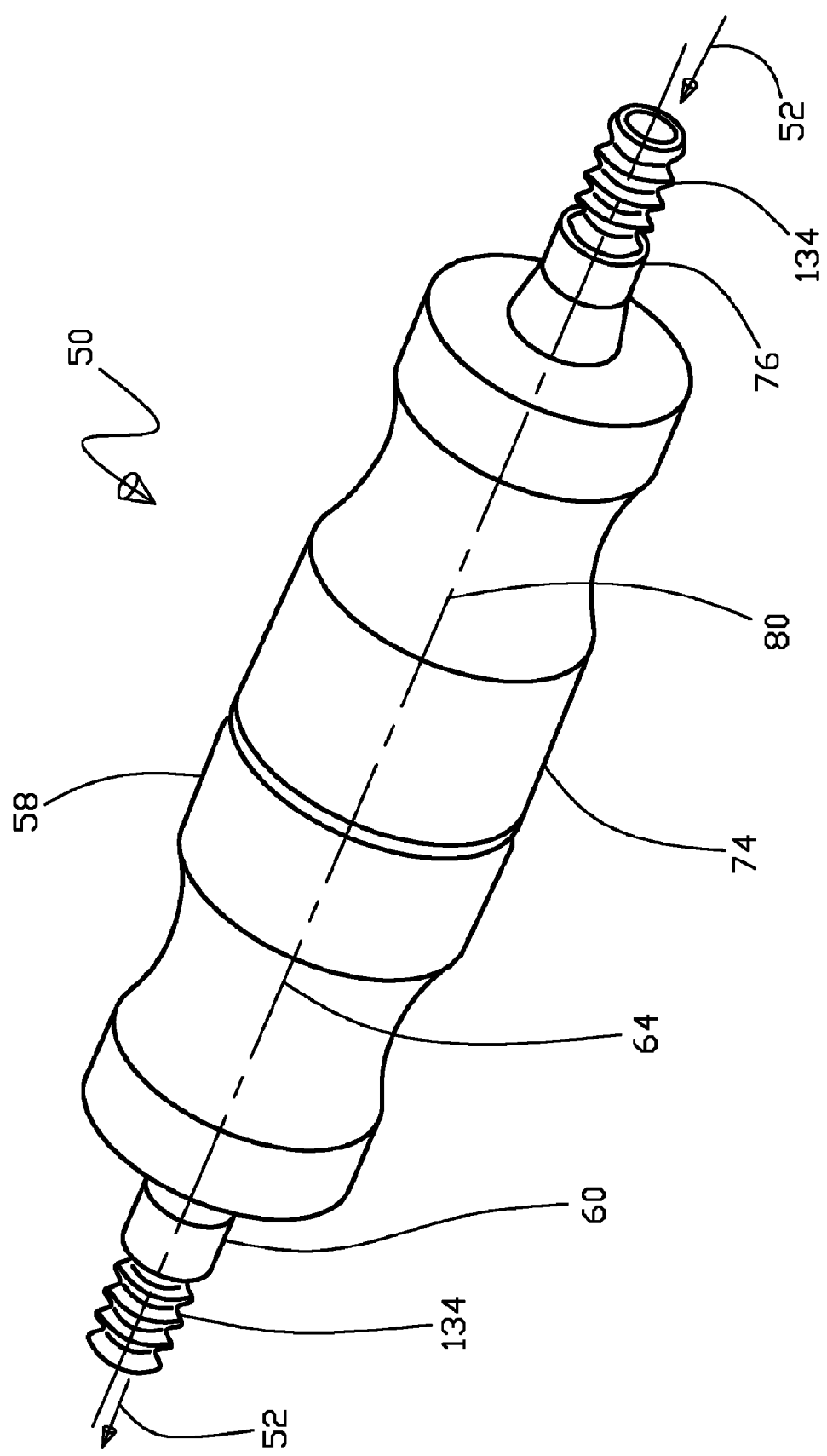
FIG. 2 is a perspective view of the fluid connector with the male housing and female housing removably engaged to one another, shown as being adapted for the threaded fluid line interface.
Figure 3:
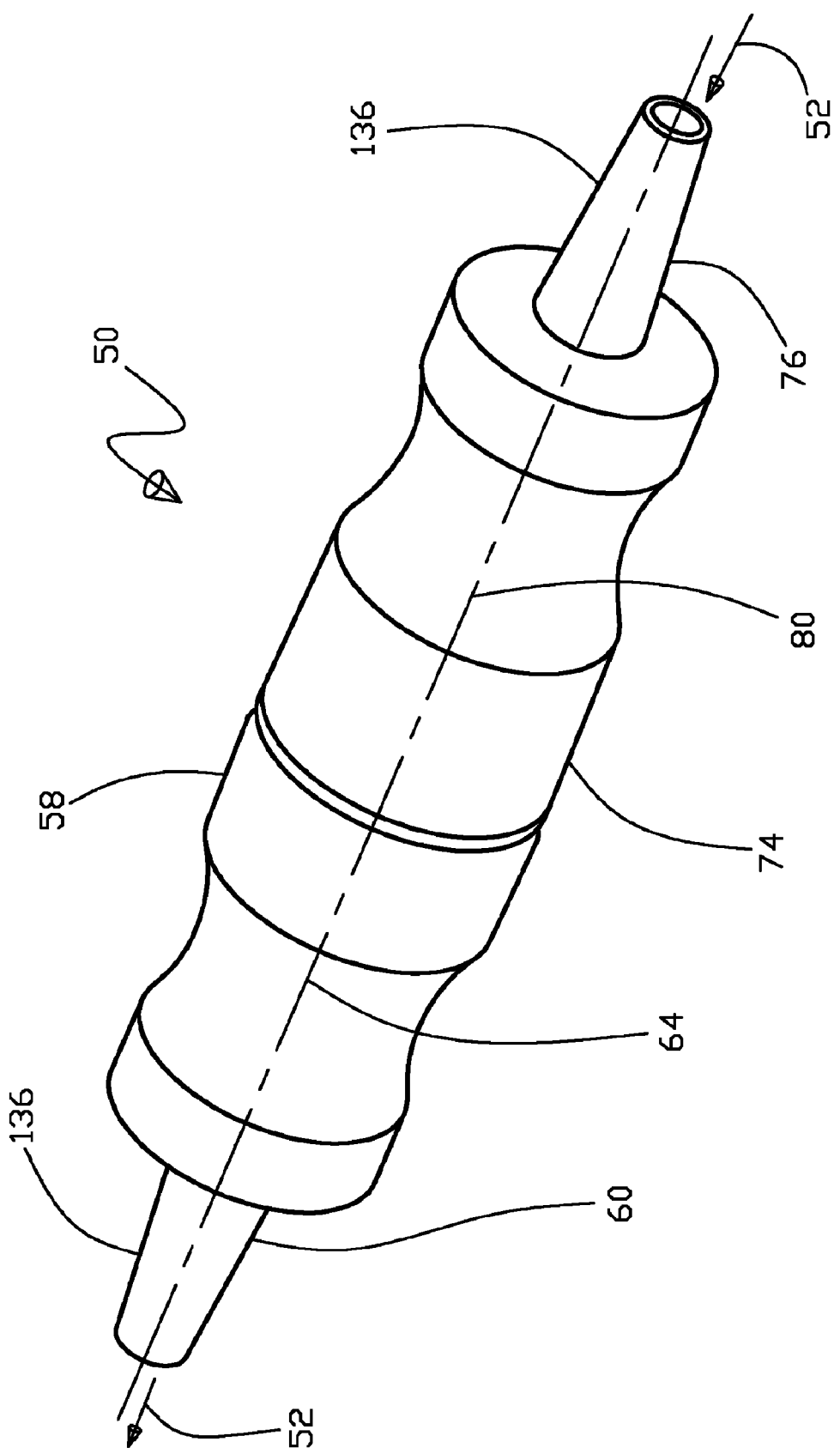
FIG. 3 is a perspective view of the fluid connector with the male housing and female housing removably engaged to one another, shown as being adapted for the luer fluid line interface.
Figure 4:
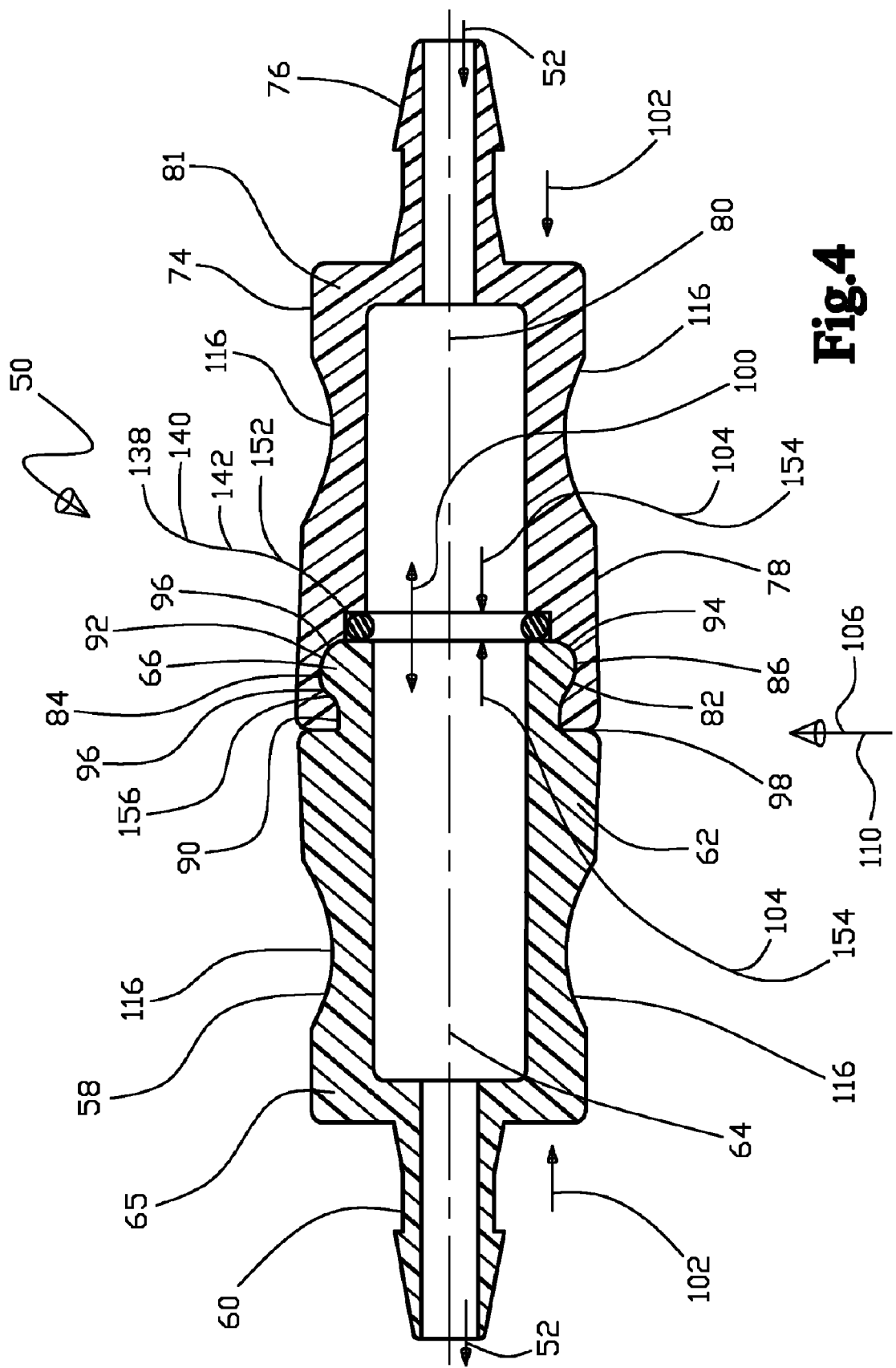
FIG. 4 is a cross sectional view of the fluid connector with the male housing and female housing removably engaged with the face seal in the form of an o-ring.
Figure 5:
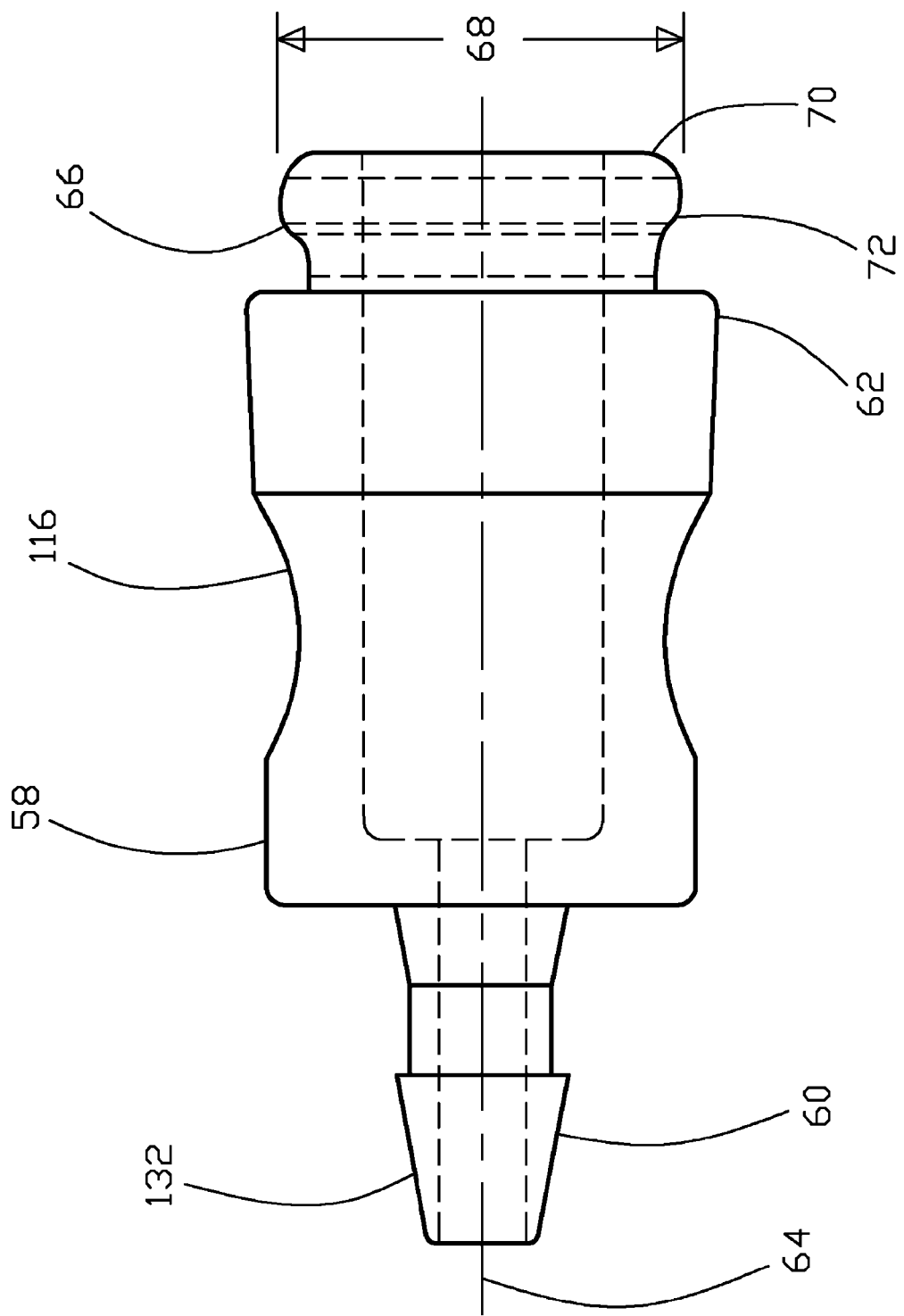
FIG. 5 is a side view of the male housing for use with the face seal including the elastically deformable ring and the adaptation for the barbed fluid line interface.

With initial reference to FIG. 1 shown is a perspective view of the fluid connector 50 with the male housing 58 and female housing 74 removably engaged 94 to one another, shown as being adapted for the barbed 132 first fluid line 54 and the second fluid line 56 interface. Continuing, FIG. 2 shows a perspective view of the fluid connector 50 with the male housing 58 and the female housing 74 removably engaged 94 to one another, shown as being adapted for the threaded 134 first fluid line 54 and the second fluid line 56 interface. Further, FIG. 3 shows a perspective view of the fluid connector 50 with the male housing 58 and female housing 74 removably engaged 94 to one another, shown as being adapted for the luer 136 first fluid line 54 and the second fluid line 56 interface. Next, FIG. 4 is a cross sectional view of the fluid connector 50 with the male housing 58 and female housing 74 removably engaged 94 with the face seal 140 in the form of an o-ring 142. Yet further, FIG. 5 is a side view of the male housing 58 for use with the face seal 140 including the elastically deformable ring 66 and the adaptation for the barbed 132 first fluid line 54 interface.

Figure 6:
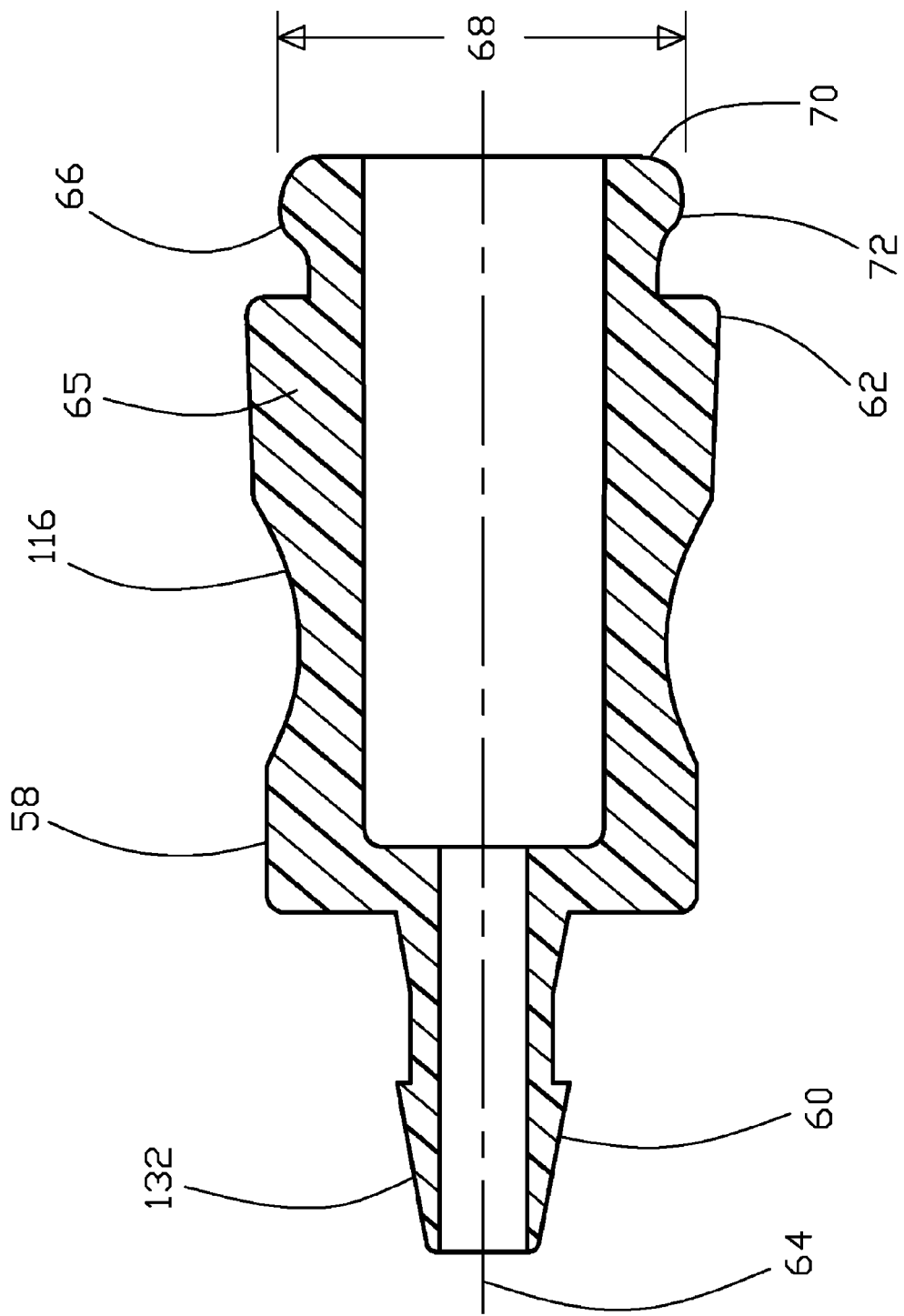
FIG. 6 is a cross sectional view of the male housing for use with the face seal including the elastic ally deformable ring and the adaptation for the barbed fluid line interface.
Figure 7:
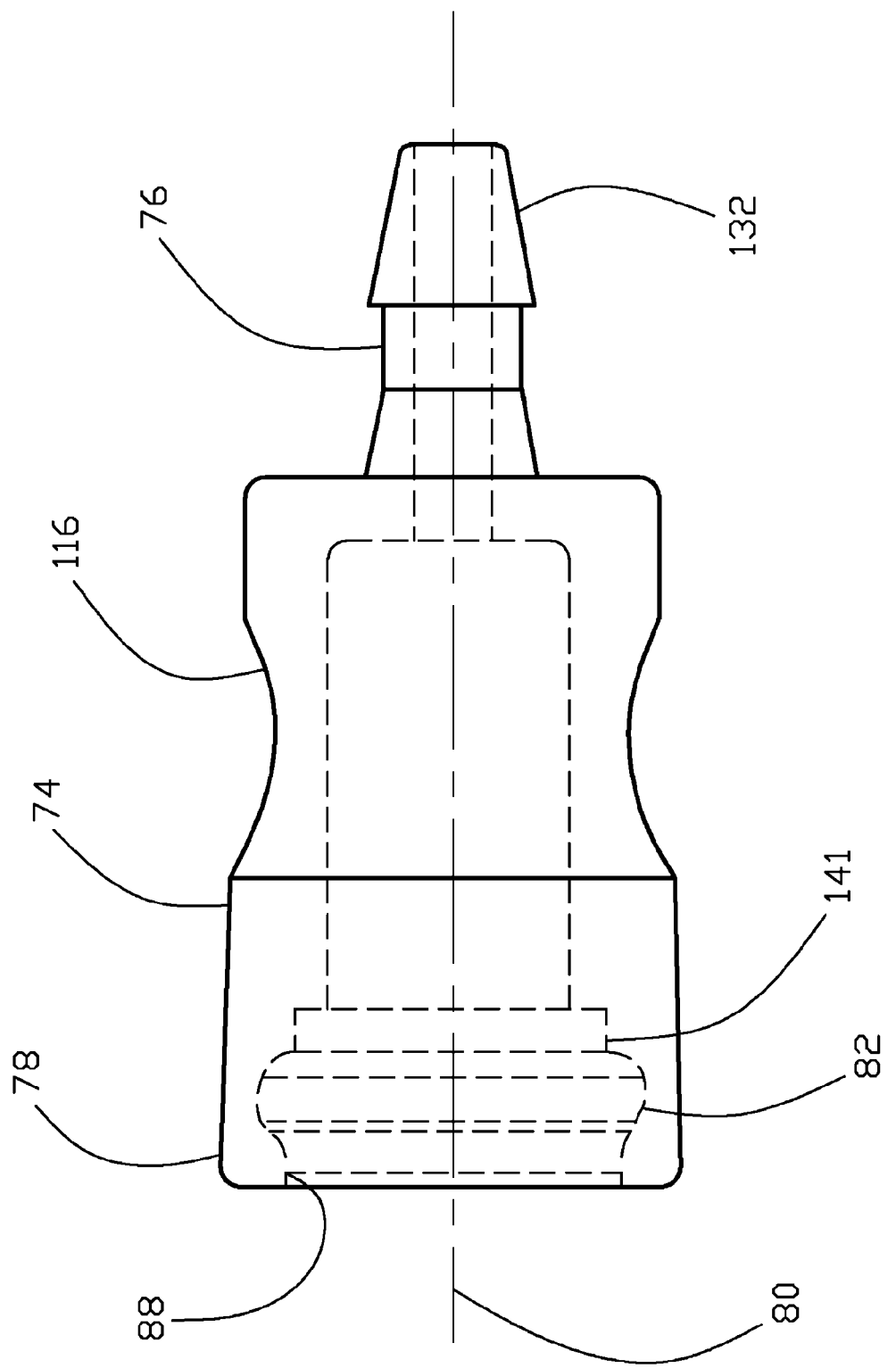
FIG. 7 is a side view of the female housing for use with the face seal including the elastically deformable annulus and the adaptation for the barbed fluid line interface.
Figure 8:
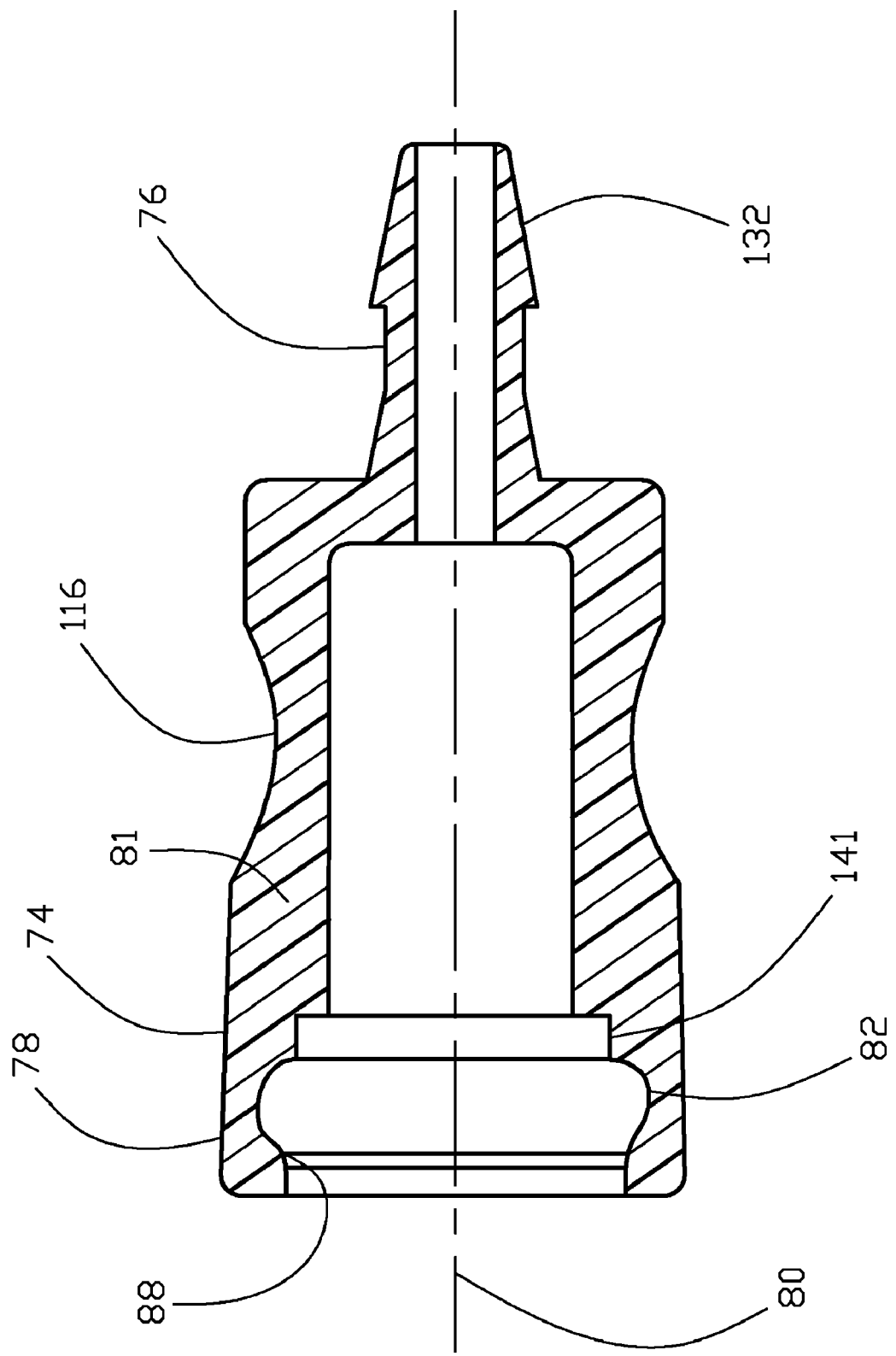
FIG. 8 is a cross sectional view of the female housing for use with the face seal including the elastically deformable annulus and the adaptation for the barbed fluid line interface.
Figure 9:
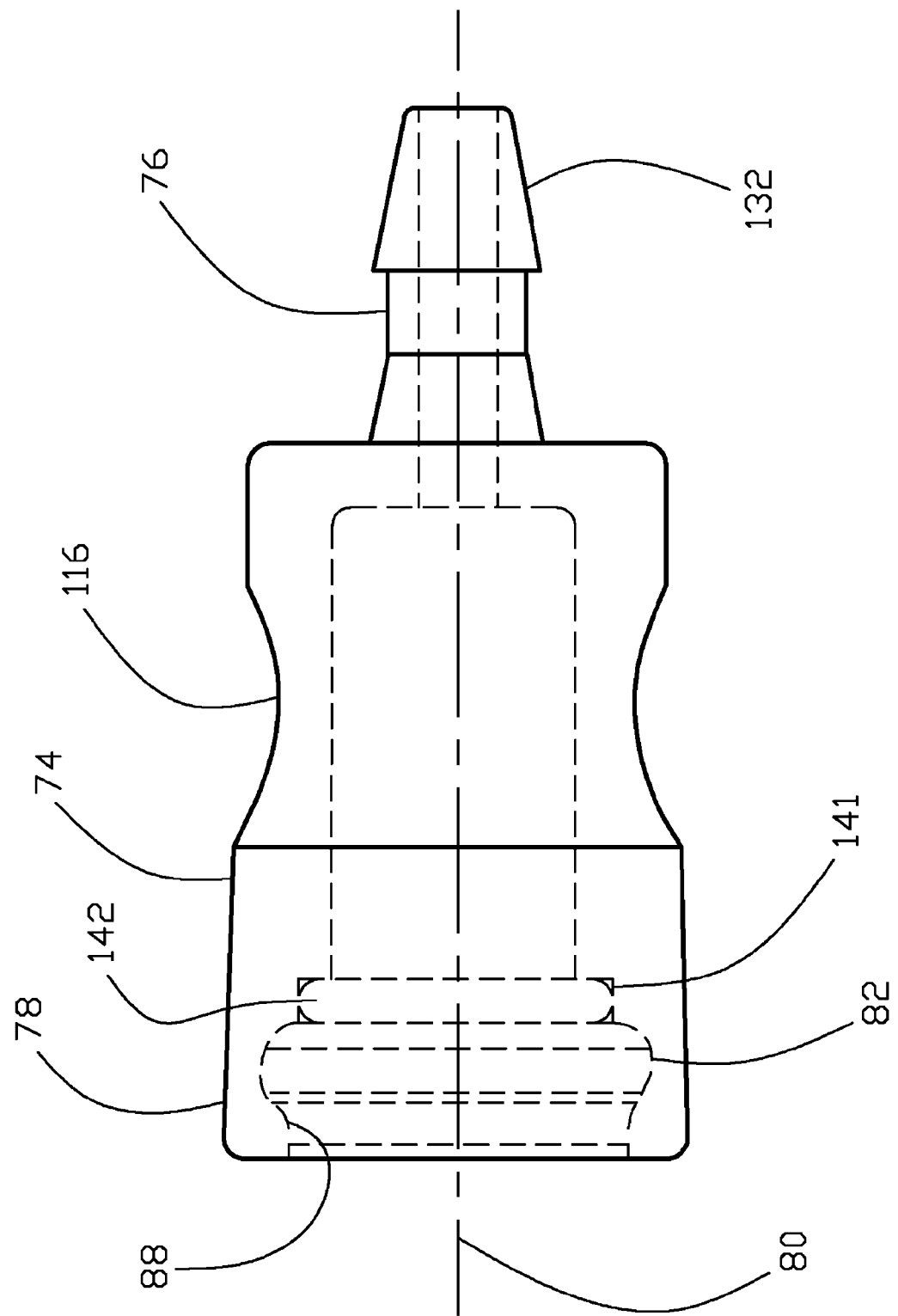
FIG. 9 is a side view of the female housing for use with the face seal in the form of an o-ring including the elastically deformable annulus and the adaptation for the barbed fluid line interface.
Figure 10:
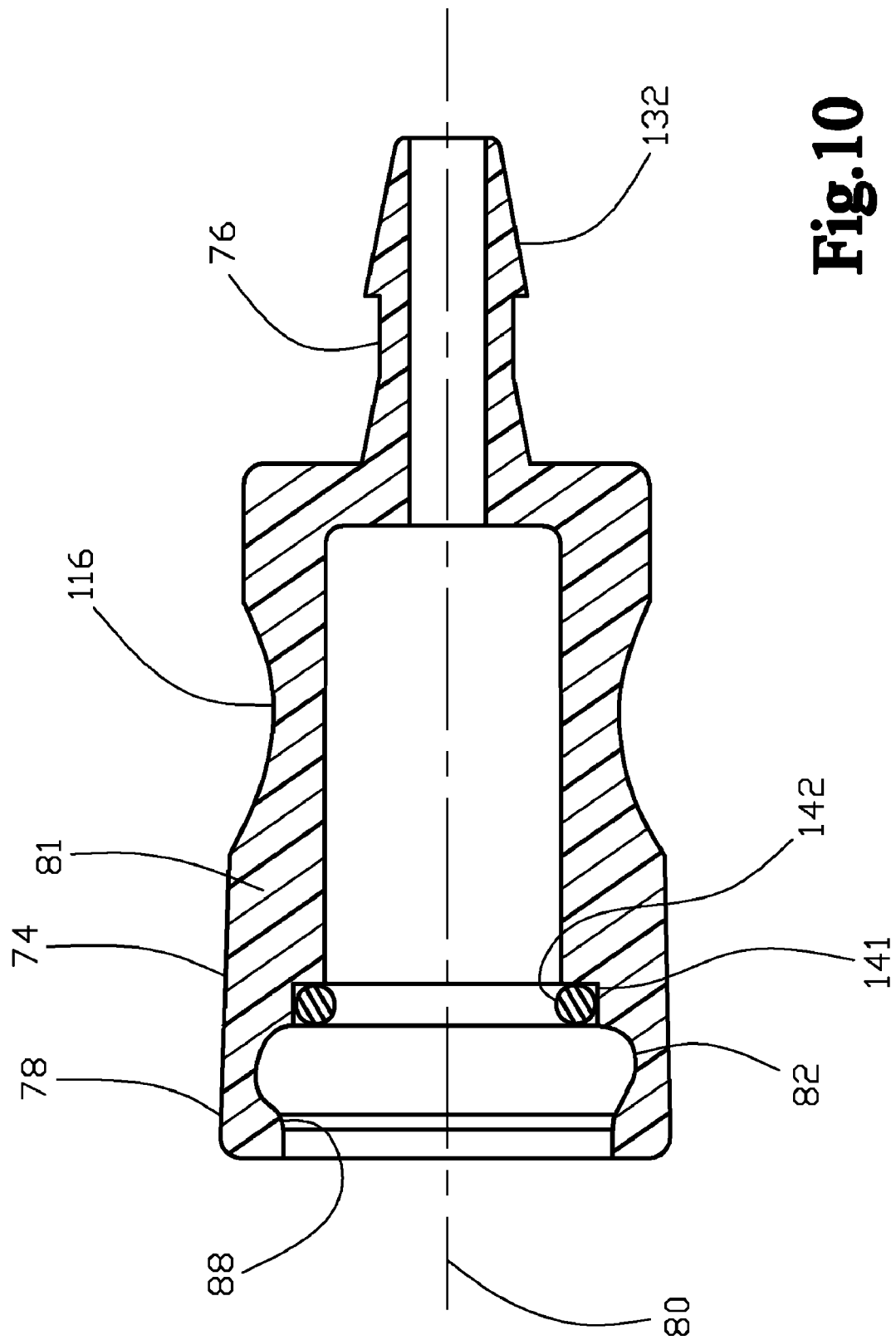
FIG. 10 is a cross sectional view of the female housing for use with the face seal in the form of the o-ring including the elastically deformable annulus and the adaptation for the barbed fluid line interface.
Figure 11:
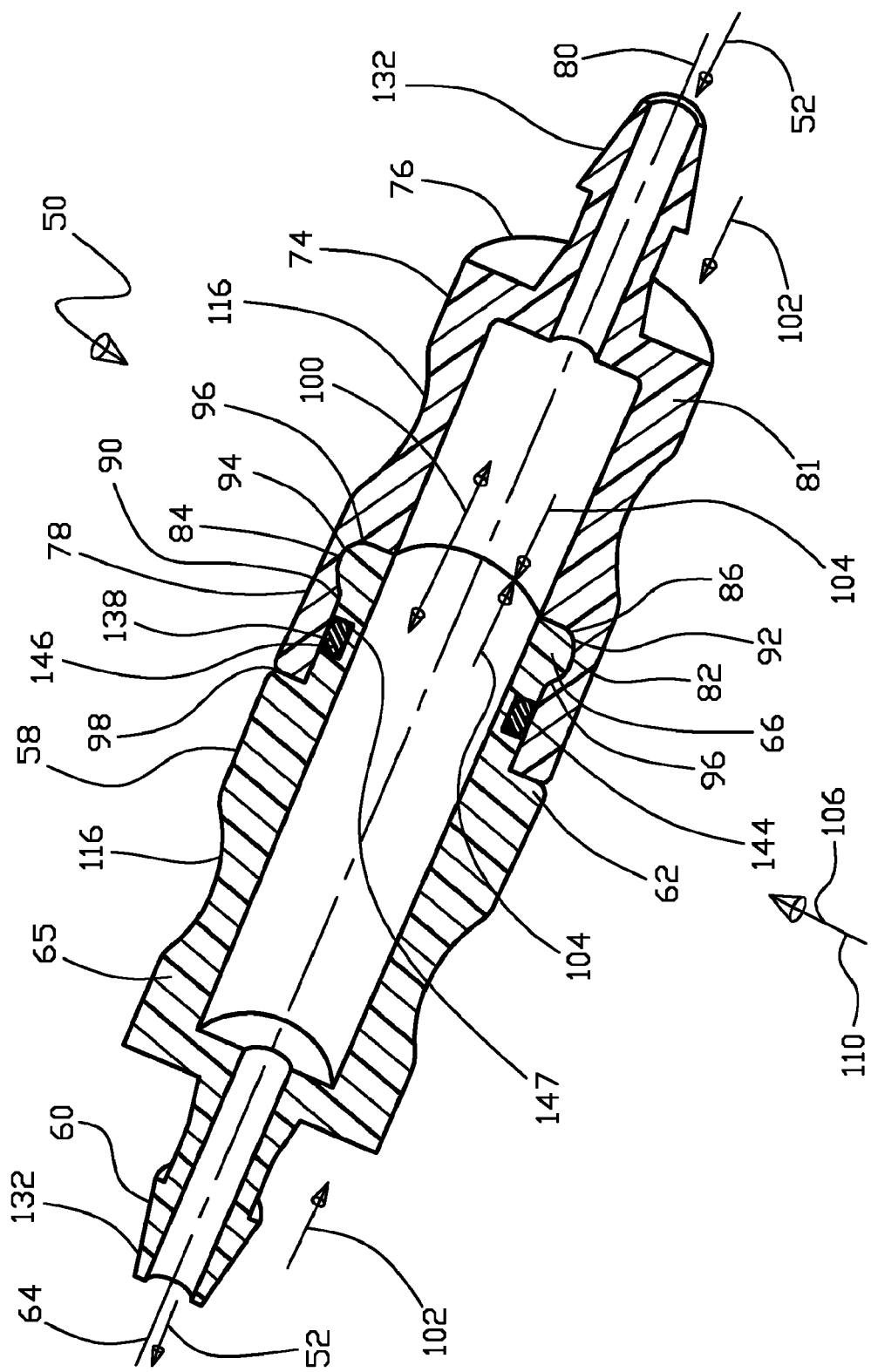
FIG. 11 is a cross sectional perspective view of the fluid connector with the male housing and female housing removably engaged with the male gland seal in the form of an o-ring.

Next continuing, FIG. 6 is a cross sectional view of the male housing 58 for use with the face seal 140 including the elastically deformable ring 66 and the adaptation for the barbed 132 first fluid line 54 interface. Further, FIG. 7 is a side view of the female housing 74 for use with the face seal 140 including the elastically deformable annulus 82 and the adaptation for the barbed 132 second fluid line 56 interface. Moving to FIG. 8 is a cross sectional view of the female housing 74 for use with the face seal 140 including the elastically deformable annulus 82 and the adaptation for the barbed 132 second fluid line 56 interface. Onward to FIG. 9 shown is a side view of the female housing 74 for use with the face seal 140 in the form of an o-ring 142 including the elastically deformable annulus 82 and the adaptation for the barbed 132 second fluid line 56 interface. Yet further, FIG. 10 is a cross sectional view of the female housing 74 for use with the face seal 140 in the form of the o-ring 142 including the elastically deformable annulus 82 and the adaptation for the barbed 132 second fluid line 56 interface. Continuing, FIG. 11 is a cross sectional perspective view of the fluid connector 50 with the male housing 58 and female housing 74 removably engaged 94 with the male gland seal 144 in the form of an o-ring 146.

Figure 12:
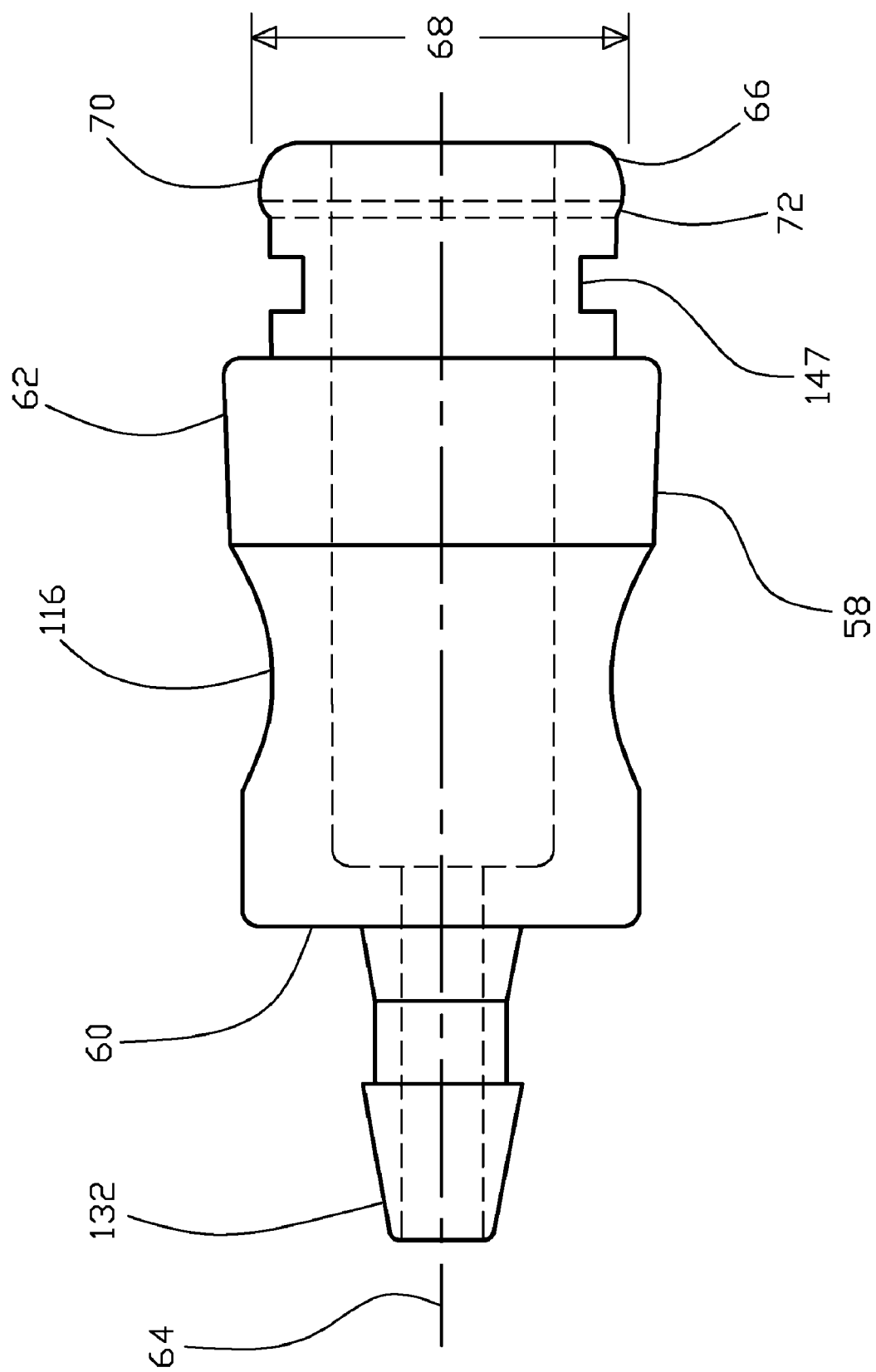
FIG. 12 is a side view of the male housing for use with the male gland seal with the channel including the elastically deformable ring and the adaptation for the barbed fluid line interface.
Figure 13:
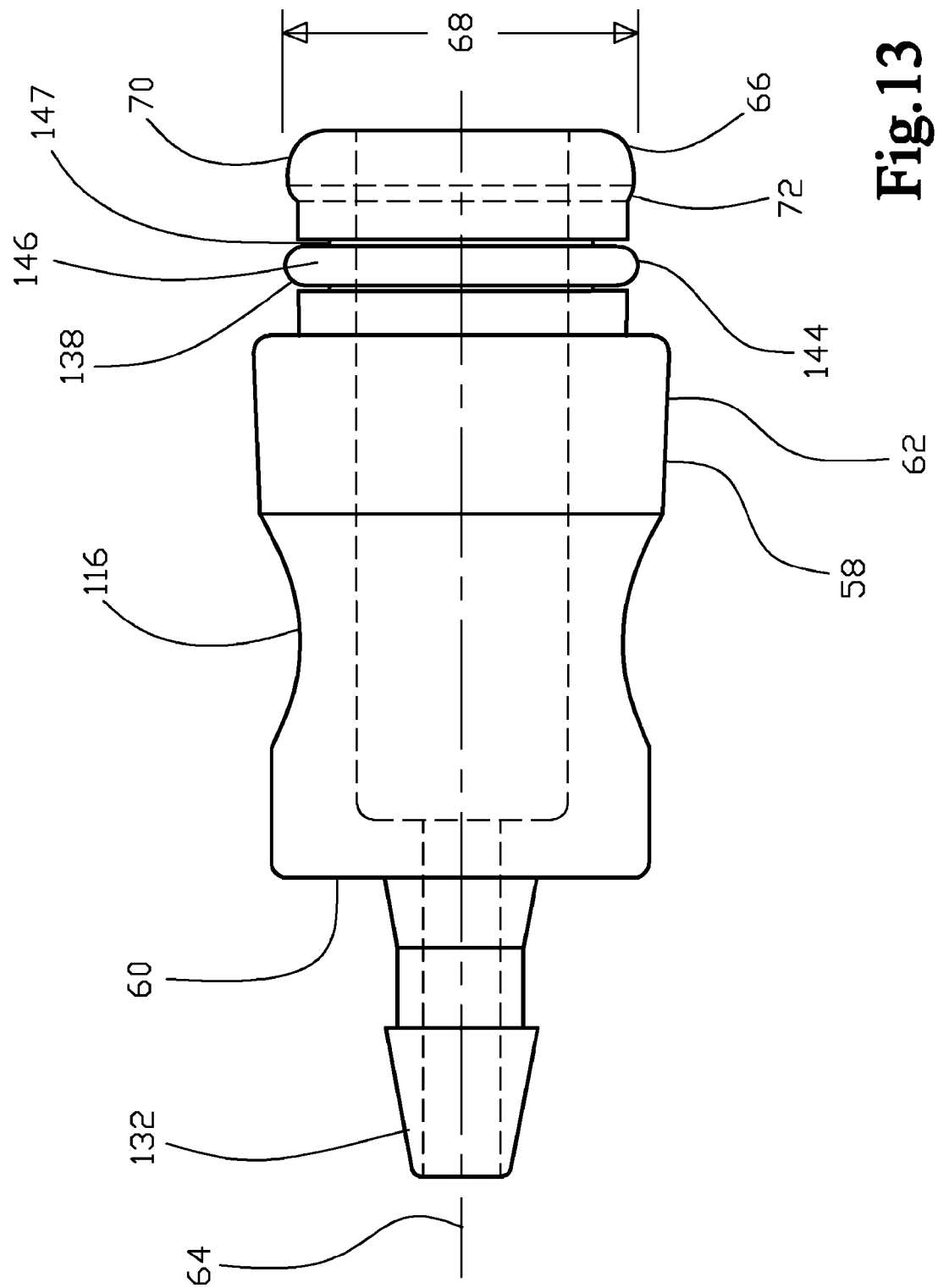
FIG. 13 is a side view of the male housing for use with the male gland seal in the form on an o-ring including the elastically deformable ring and the adaptation for the barbed fluid line interface.
Figure 14:
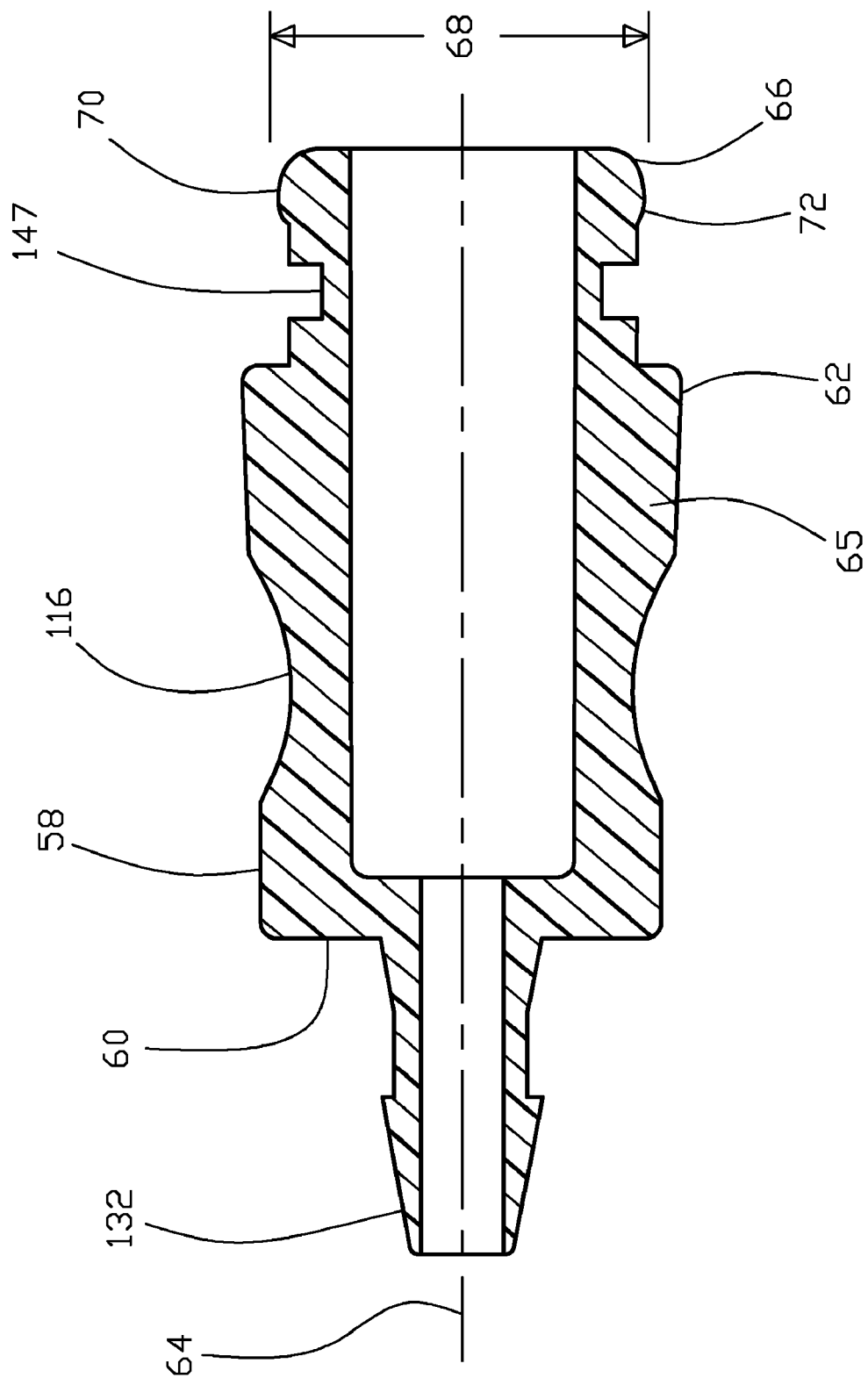
FIG. 14 is a cross sectional view of the male housing for use with the male gland seal with the channel including the elastically deformable ring and the adaptation for the barbed fluid line interface.
Figure 15:
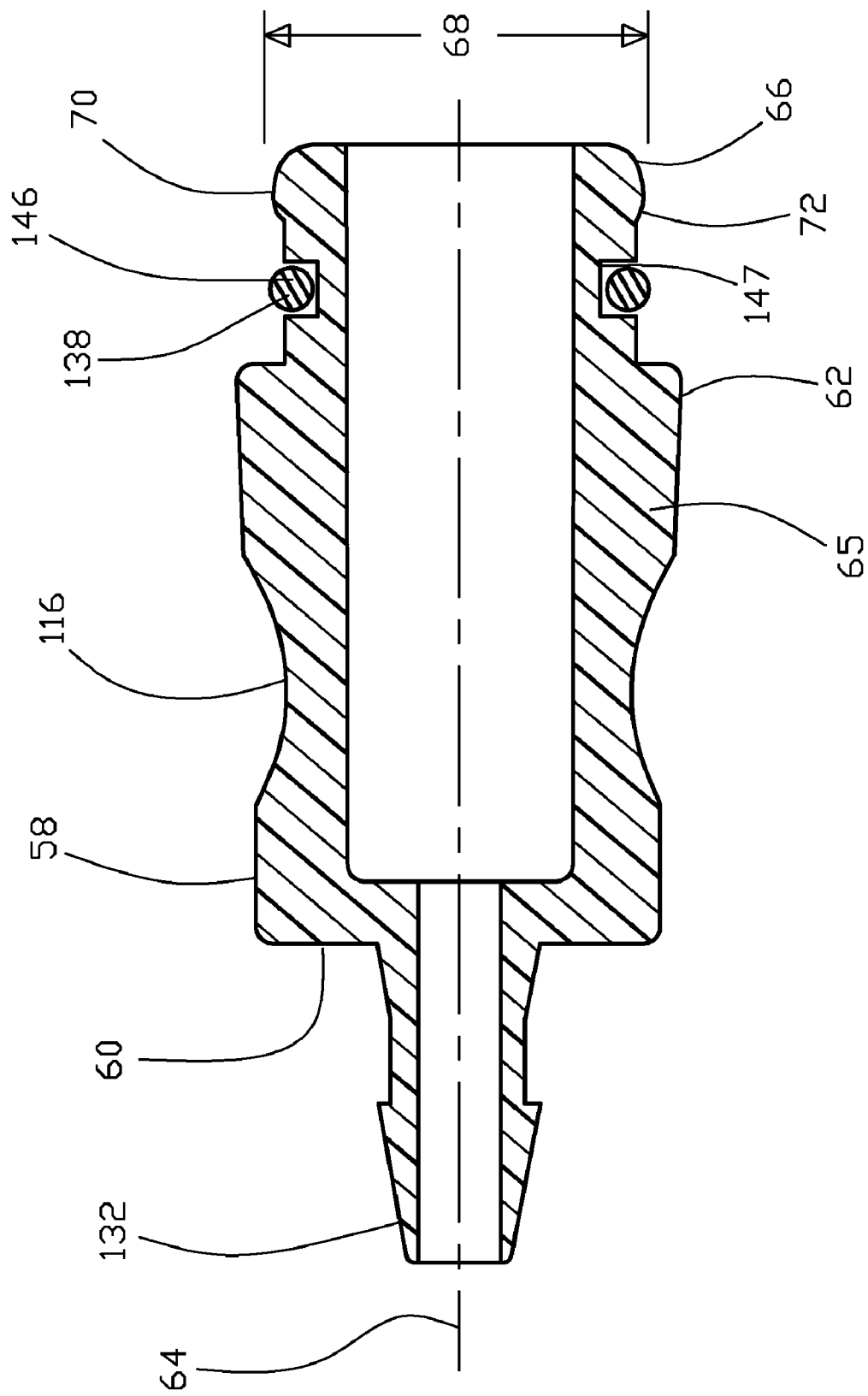
FIG. 15 is a cross sectional view of the male housing for use with the male gland seal in the form of the o-ring including the elastically deformable ring and the adaptation for the barbed fluid line interface.
Figure 16:
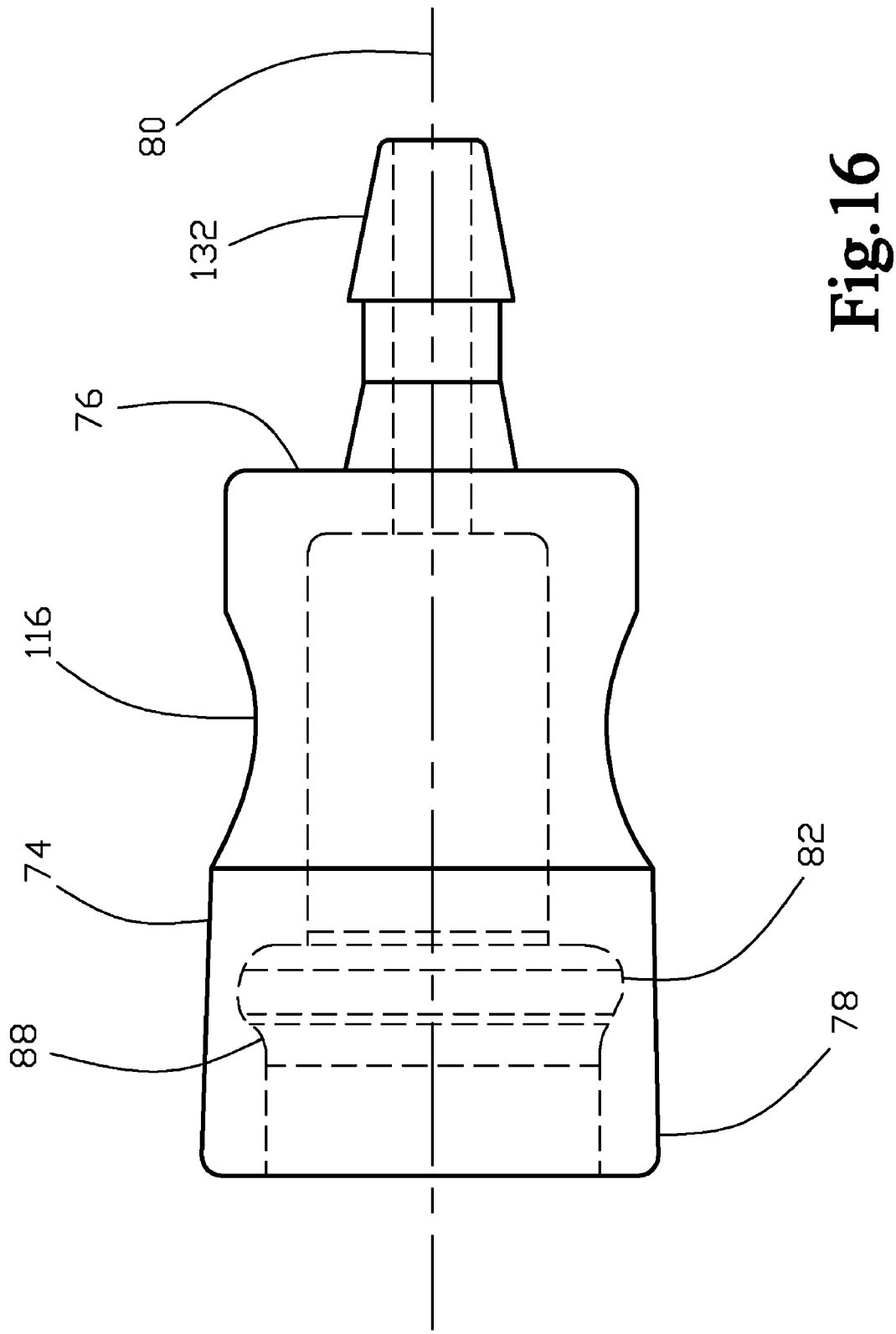
FIG. 16 is a side view of the female housing for use with the male gland seal including the elastically deformable annulus and the adaptation for the barbed fluid line interface.
Figure 17:
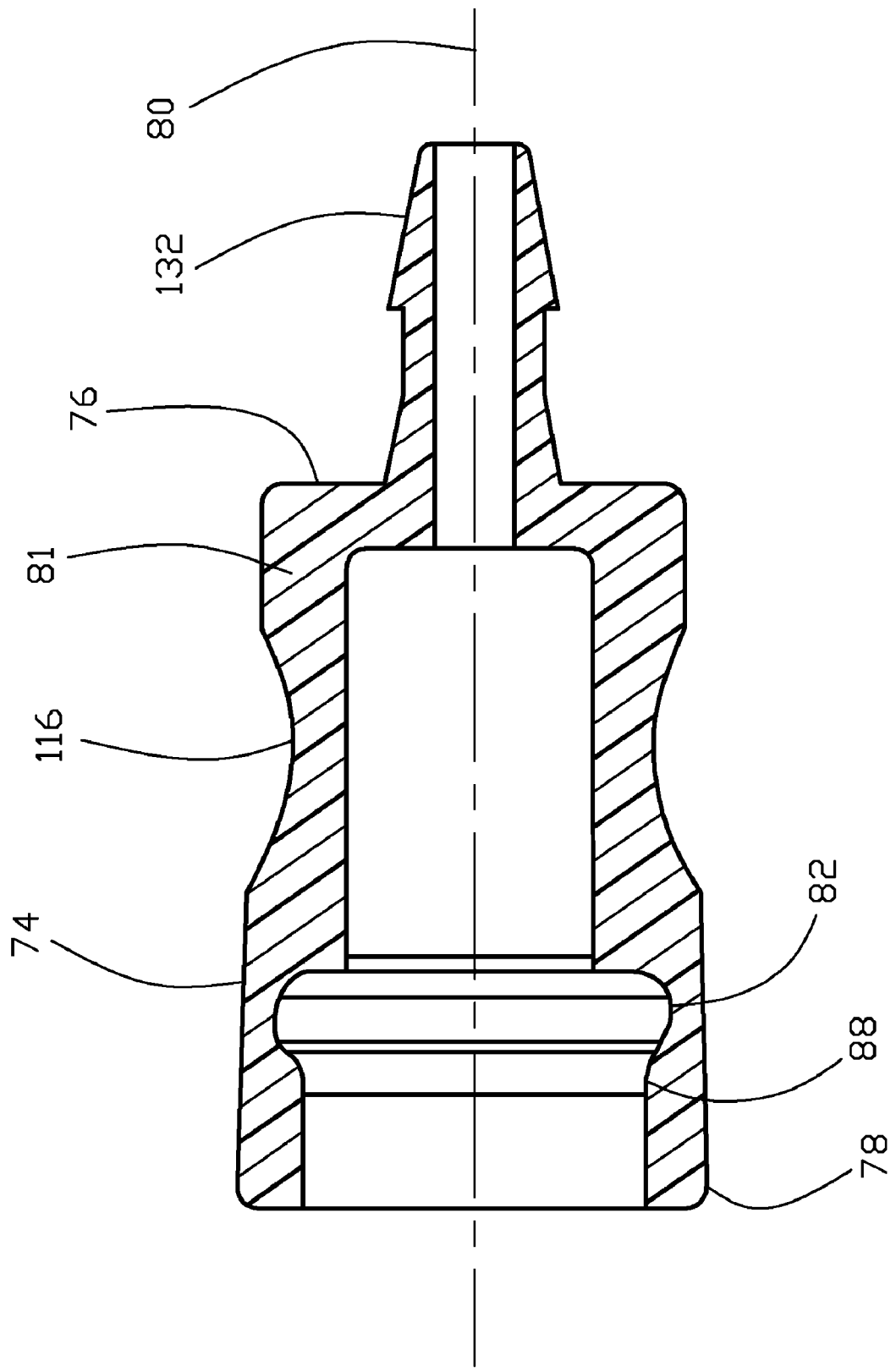
FIG. 17 is a cross sectional view of the female housing for use with the male gland seal including the elastically deformable annulus and the adaptation for the barbed fluid line interface.

Moving on, FIG. 12 shows a side view of the male housing 58 for use with the male gland seal 144 with the channel 147 including the elastically deformable ring 66 and the adaptation for the barbed 132 first fluid line 54 interface. Next, FIG. 13 is a side view of the male housing 58 for use with the male gland seal 144 in the form on an o-ring 146 including the elastically deformable ring 66 and the adaptation for the barbed 132 first fluid line 54 interface. Continuing, FIG. 14 is a cross sectional view of the male housing 58 for use with the male gland seal 144 with the channel 147 including the elastically deformable ring 66 and the adaptation for the barbed 132 first fluid line 54 interface. Yet further, FIG. 15 is a cross sectional view of the male housing 58 for use with the male gland seal 144 in the form of the o-ring 146 including the elastically deformable ring 66 and the adaptation for the barbed 132 first fluid line 54 interface. Looking to FIG. 16 is a side view of the female housing 74 for use with the male gland seal 144 including the elastically deformable annulus 82 and the adaptation for the barbed 132 second fluid line 56 interface. Moving again onward, FIG. 17 is a cross sectional view of the female housing 74 for use with the male gland seal 144 including the elastically deformable annulus 82 and the adaptation for the barbed 132 second fluid line 56 interface.

Figure 18:
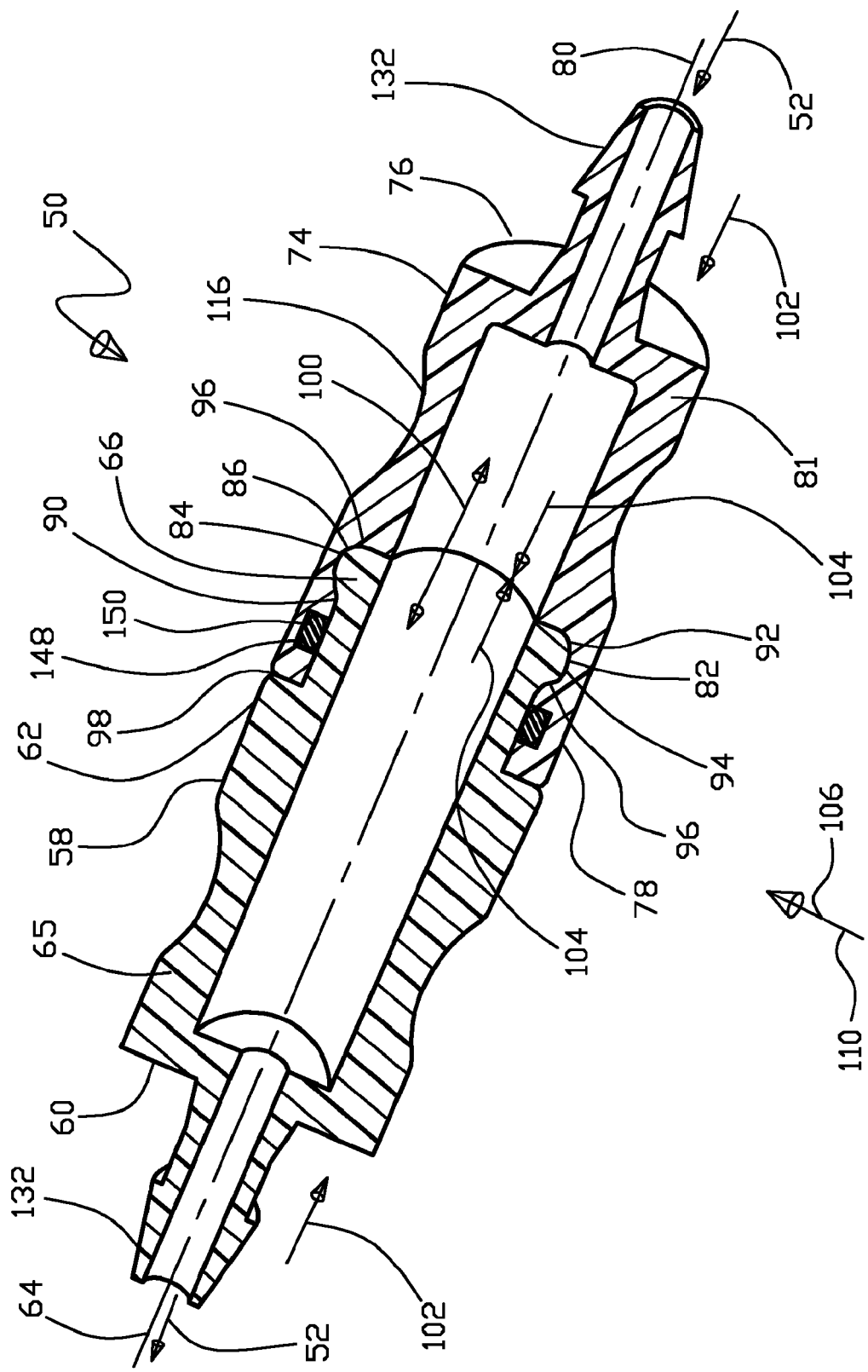
FIG. 18 is a cross sectional perspective view of the fluid connector with the male housing and female housing removably engaged with the female gland seal in the form of an o-ring.
Figure 19:
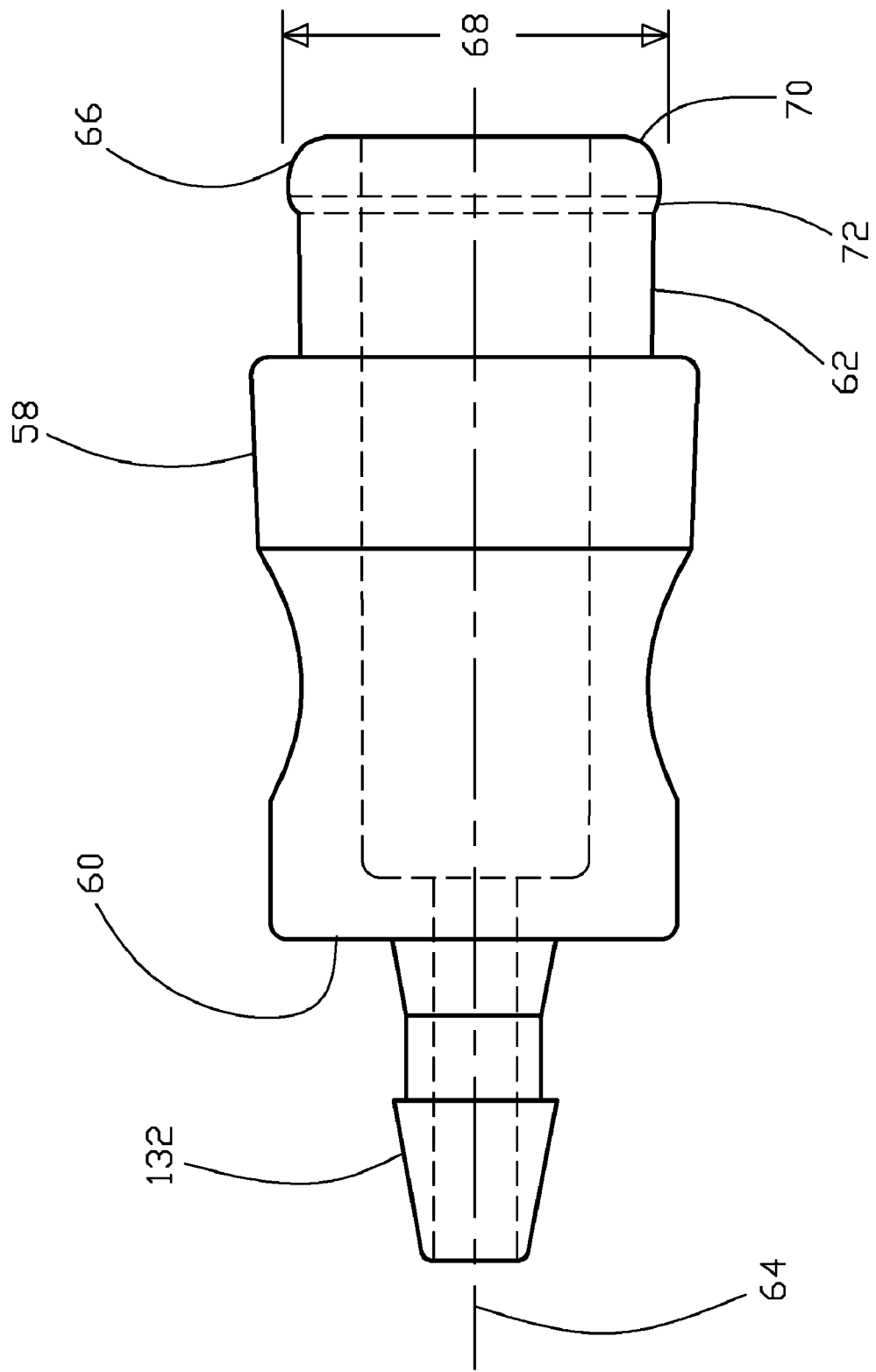
FIG. 19 is a side view of the male housing for use with the female gland seal including the elastically deformable ring and the adaptation for the barbed fluid line interface.
Figure 20:
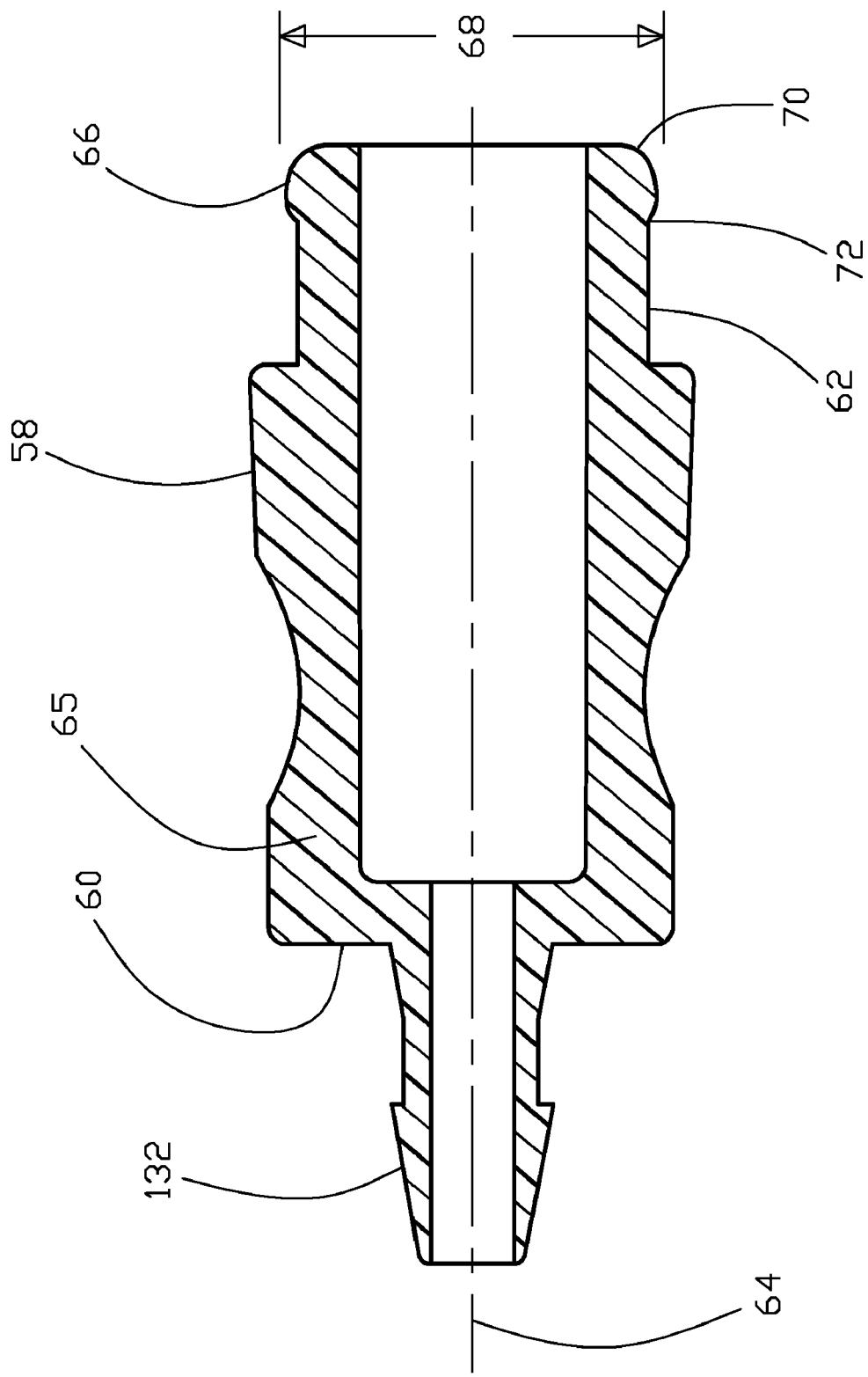
FIG. 20 is a cross sectional view of the male housing for use with the female gland seal including the elastically deformable ring and the adaptation for the barbed fluid line interface.
Figure 21:
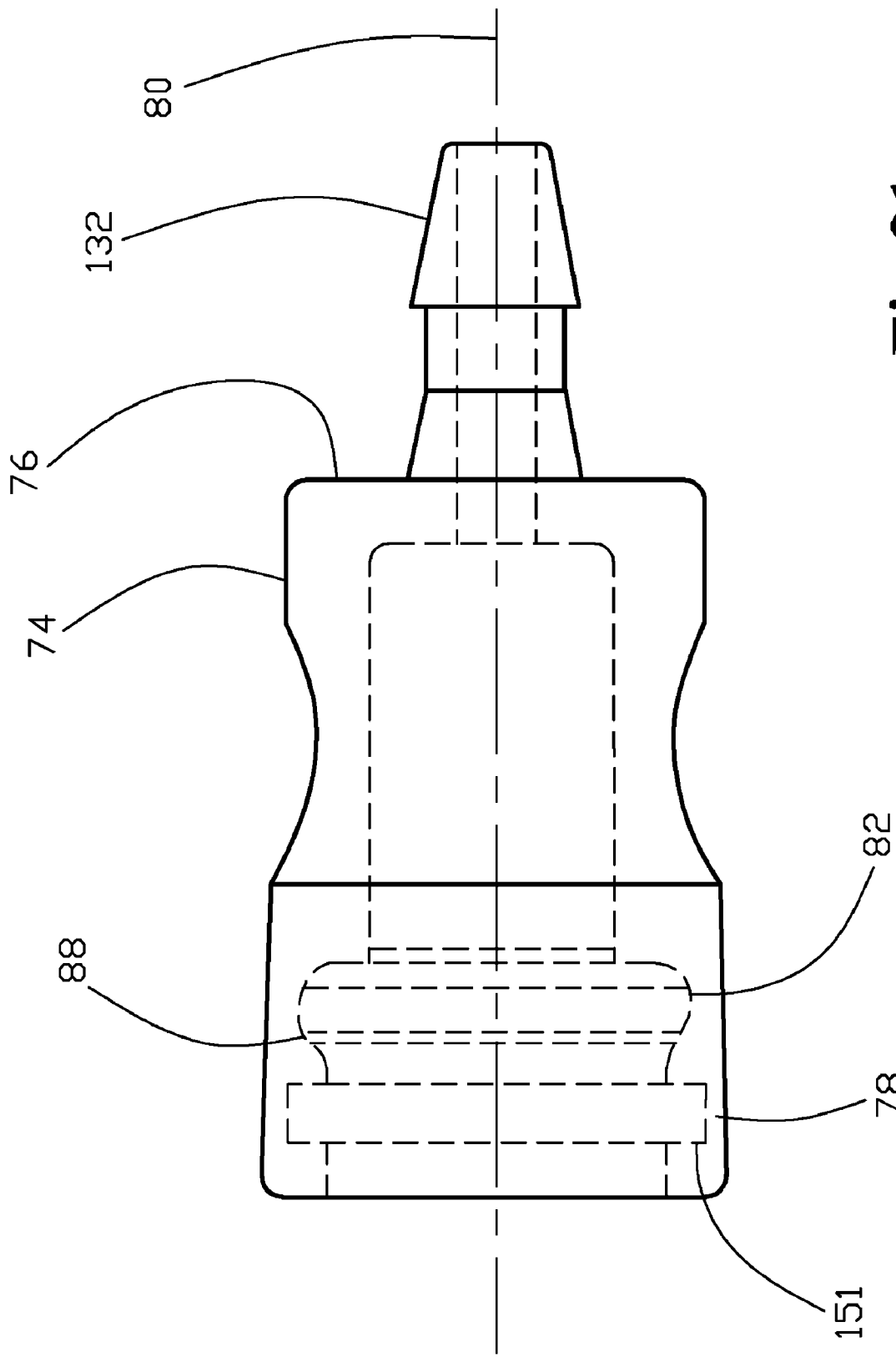
FIG. 21 is a side view of the female housing for use with the female gland seal with the channel including the elastically deformable annulus and the adaptation for the barbed fluid line interface.
Figure 22:
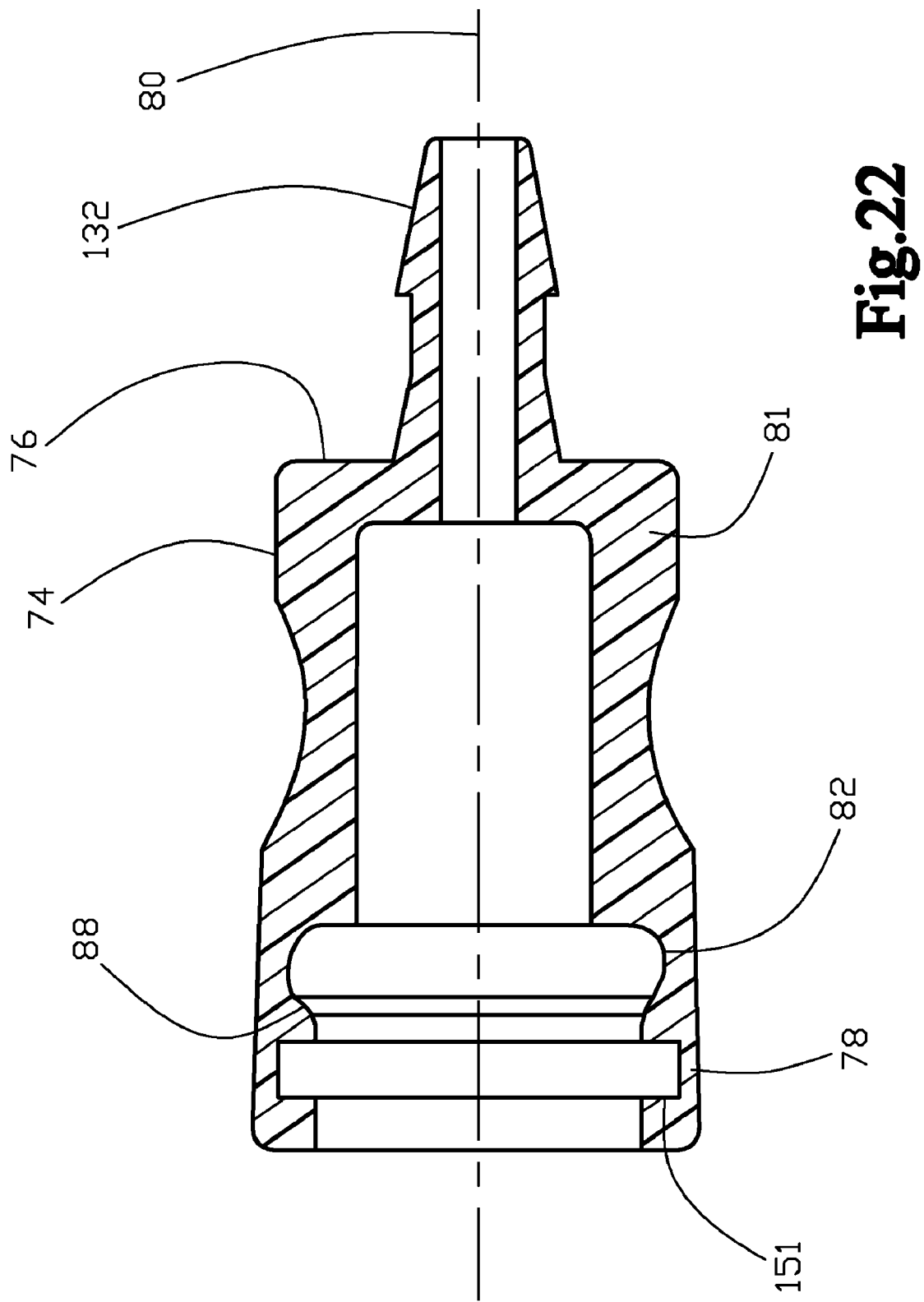
FIG. 22 is a cross sectional view of the female housing for use with the female gland seal with the channel including the elastically deformable annulus and the adaptation for the barbed fluid line interface.
Figure 23:
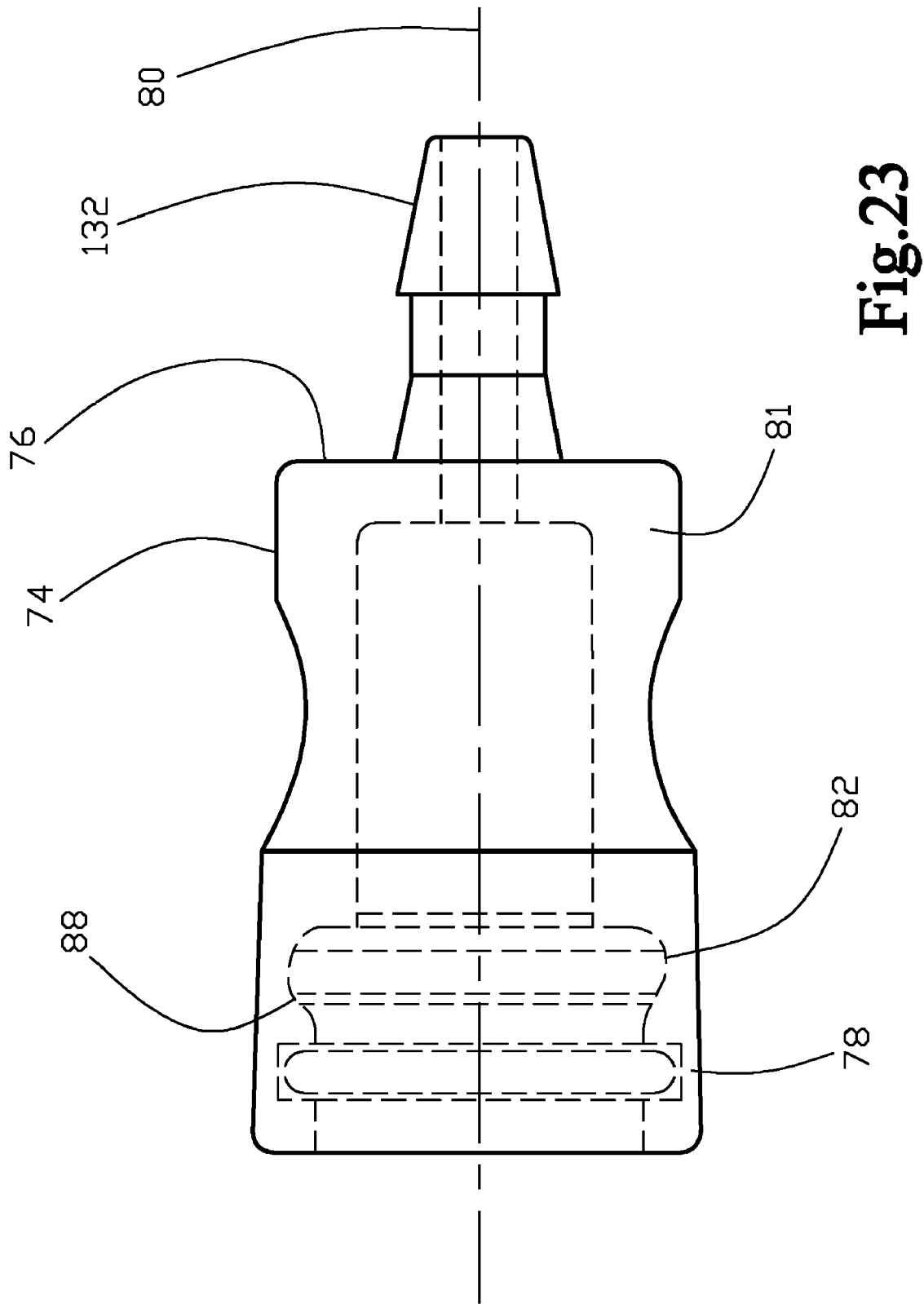
FIG. 23 is a side view of the female housing for use with the female gland seal in the form of an o-ring including the elastically deformable annulus and the adaptation for the barbed fluid line interface.
Figure 24:
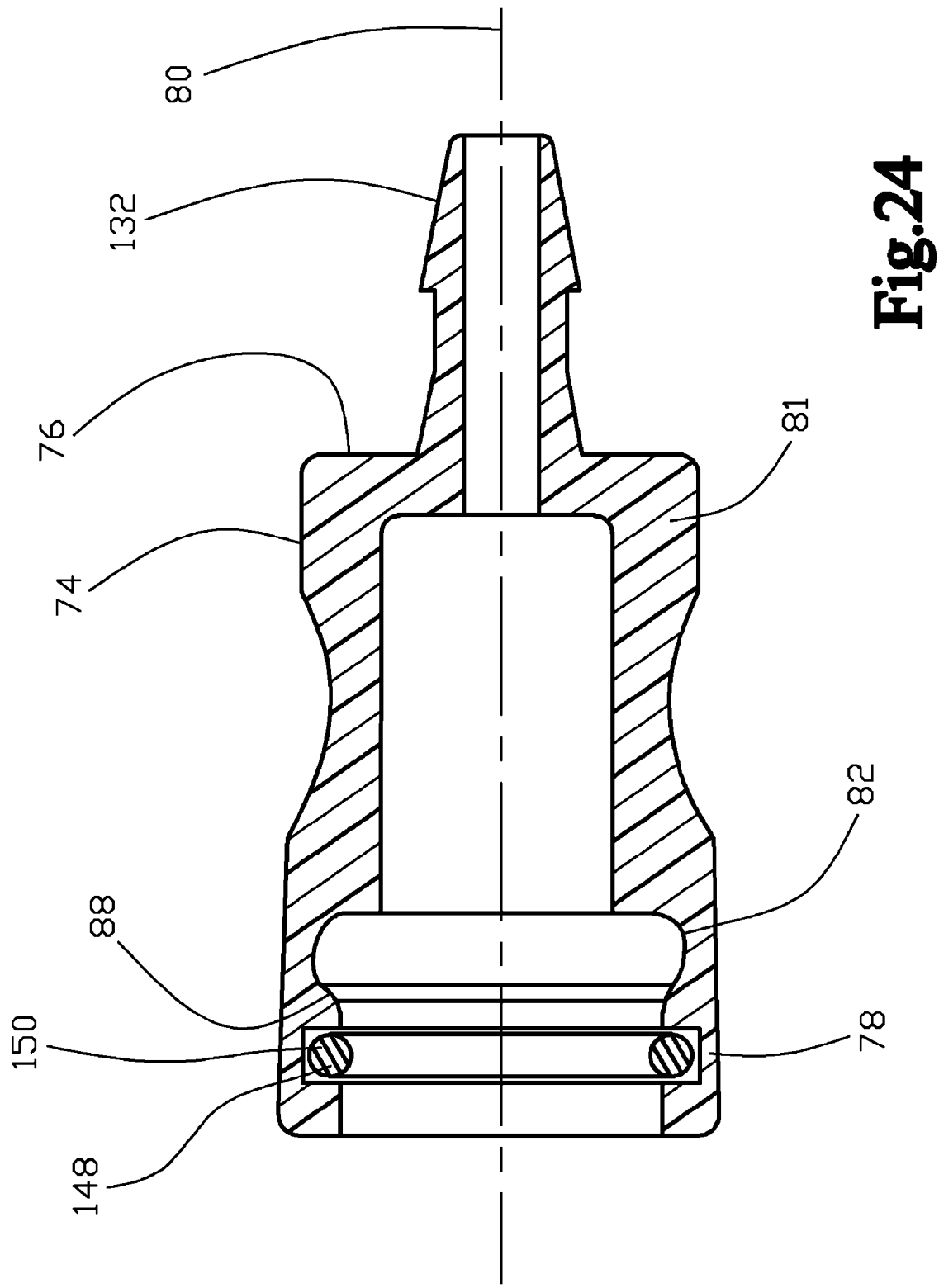
FIG. 24 is a cross sectional view of the female housing for use with the female gland seal in the form of an o-ring including the elastically deformable annulus and the adaptation for the barbed fluid line interface.

Next FIG. 18 is a cross sectional perspective view of the fluid connector 50 with the male housing 58 and female housing 74 removably engaged 84 with the female gland seal 148 in the form of an o-ring 150. Further, FIG. 19 is a side view of the male housing 58 for use with the female gland seal 148 including the elastically deformable ring 66 and the adaptation for the barbed 132 first fluid line 54 interface. Furthermore, FIG. 20 is a cross sectional view of the male housing 58 for use with the female gland seal 148 including the elastically deformable ring 66 and the adaptation for the barbed 132 first fluid line 54 interface. Next, FIG. 21 is a side view of the female housing 74 for use with the female gland seal 148 with the channel 151 including the elastically deformable annulus 82 and the adaptation for the barbed 132 second fluid line 56 interface. Continuing, FIG. 22 is a cross sectional view of the female housing 74 for use with the female gland seal 148 with the channel 151 including the elastically deformable annulus 82 and the adaptation for the barbed 132 second fluid line 56 interface. Looking onward, FIG. 23 is a side view of the female housing 74 for use with the female gland seal 151 in the form of an o-ring 150 including the elastically deformable annulus 82 and the adaptation for the barbed 132 second fluid line 56 interface. Yet continuing further FIG. 24 is a cross sectional view of the female housing 74 for use with the female gland seal 151 in the form of an o-ring 150 including the elastically deformable annulus 82 and the adaptation for the barbed 132 second fluid line 56 interface.

Figure 25:
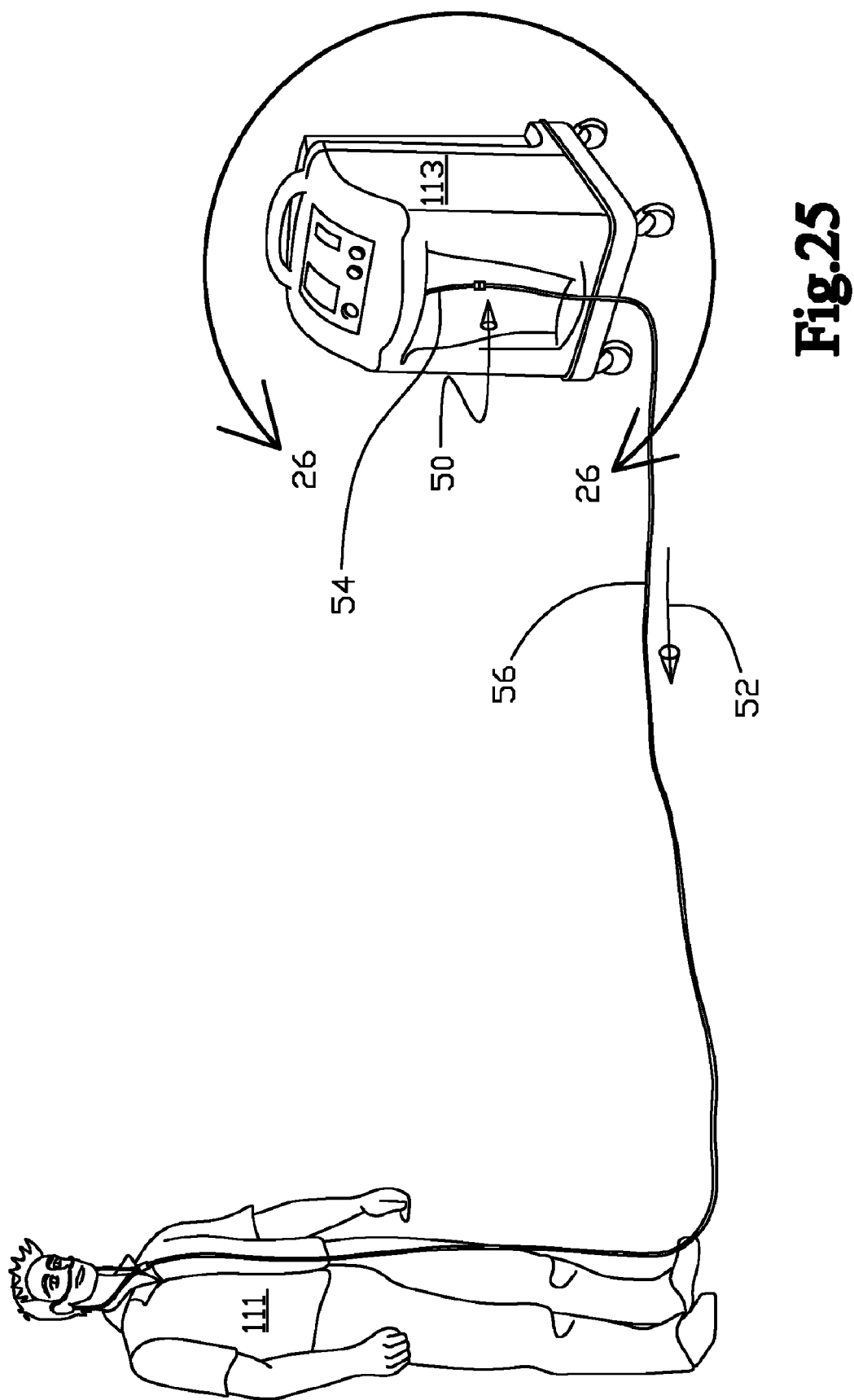
FIG. 25 shows a view of the fluid connector in use in a medical application for delivering oxygen to a human user patient via a first line, through the fluid connector, and via the second fluid line with fluid communication from an oxygen fluid provider in the medical application.
Figure 26:
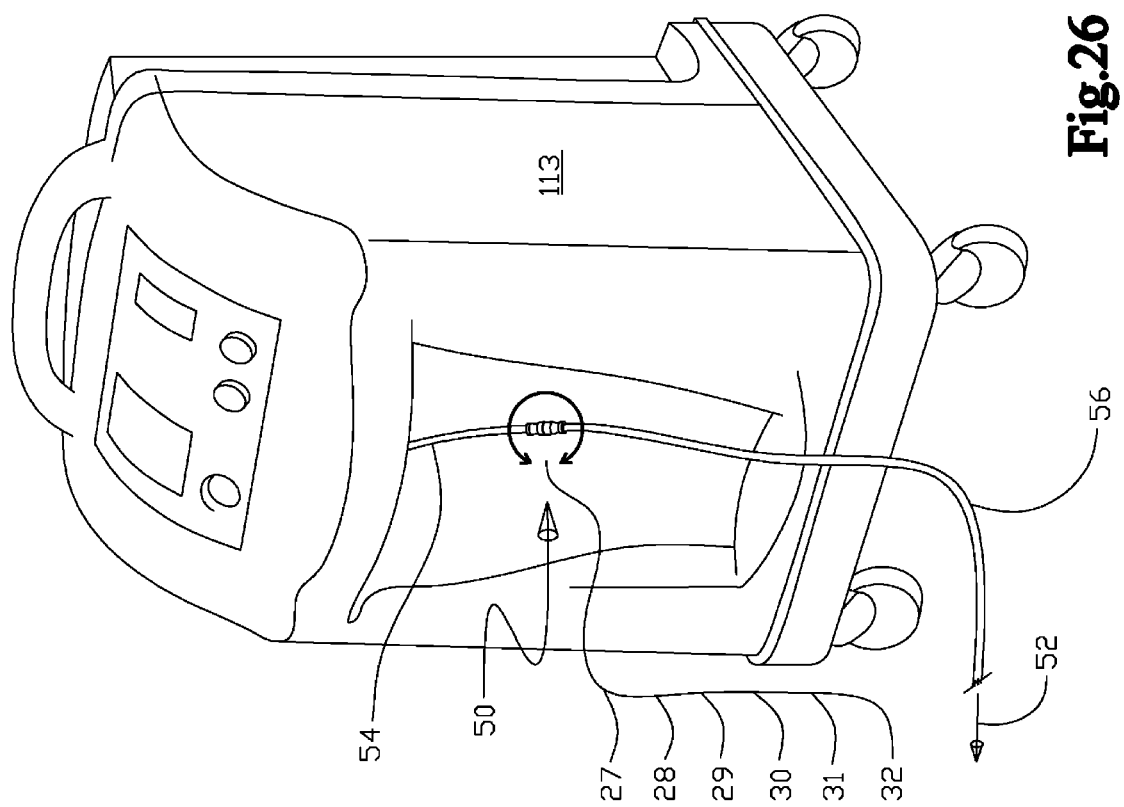
FIG. 26 shows a close up view of the fluid connector in the medical application use as taken from FIG. 25, with the oxygen fluid provider in the medical application delivering oxygen via the first line, the fluid connector, and the second line with fluid communication.
Figure 27:
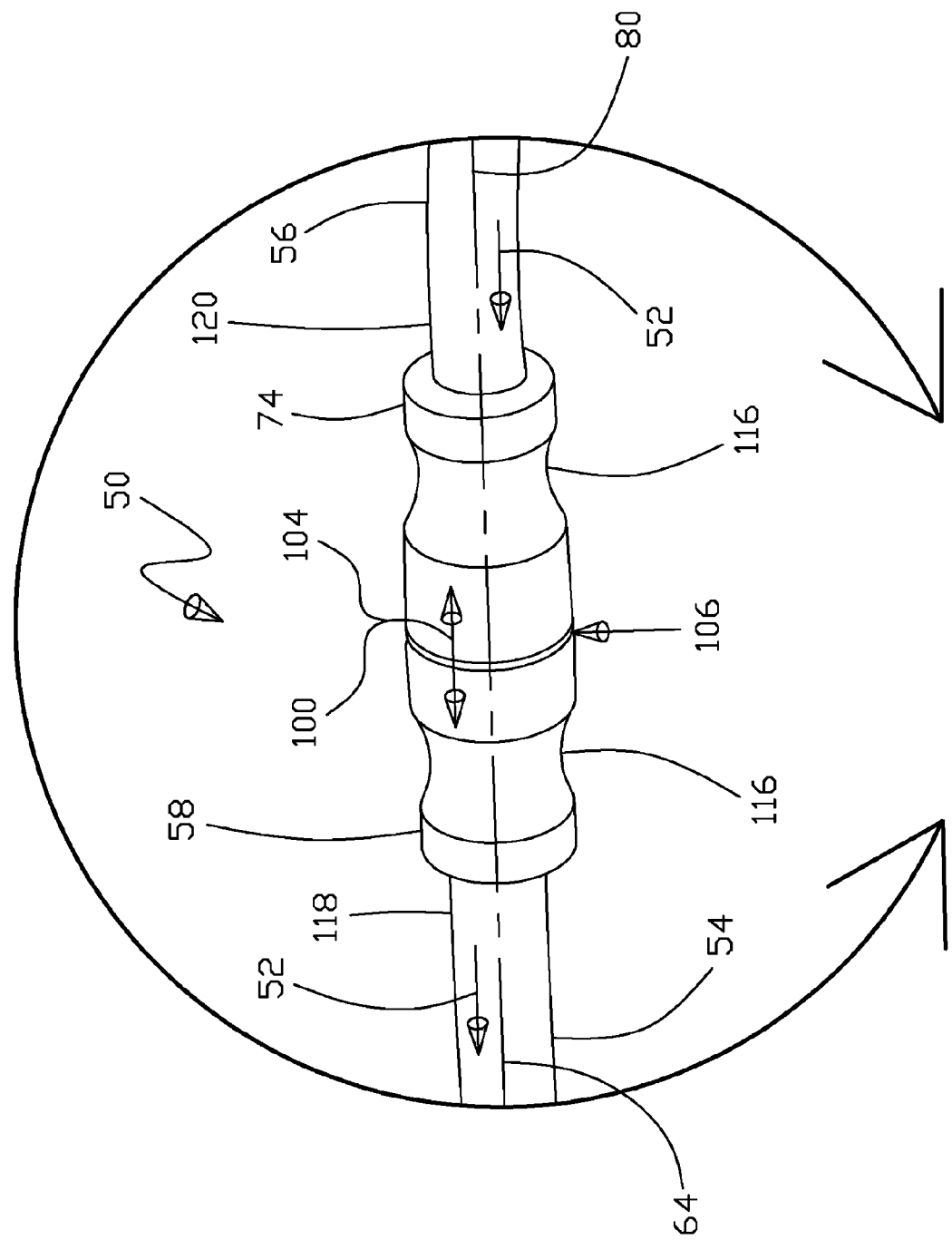
FIG. 27 shows an expanded view close up of the fluid connector in the medical application use as taken from both FIGS. 25 and 26 with the male and female housings removably engaged with the fluid communication.
Figure 28:
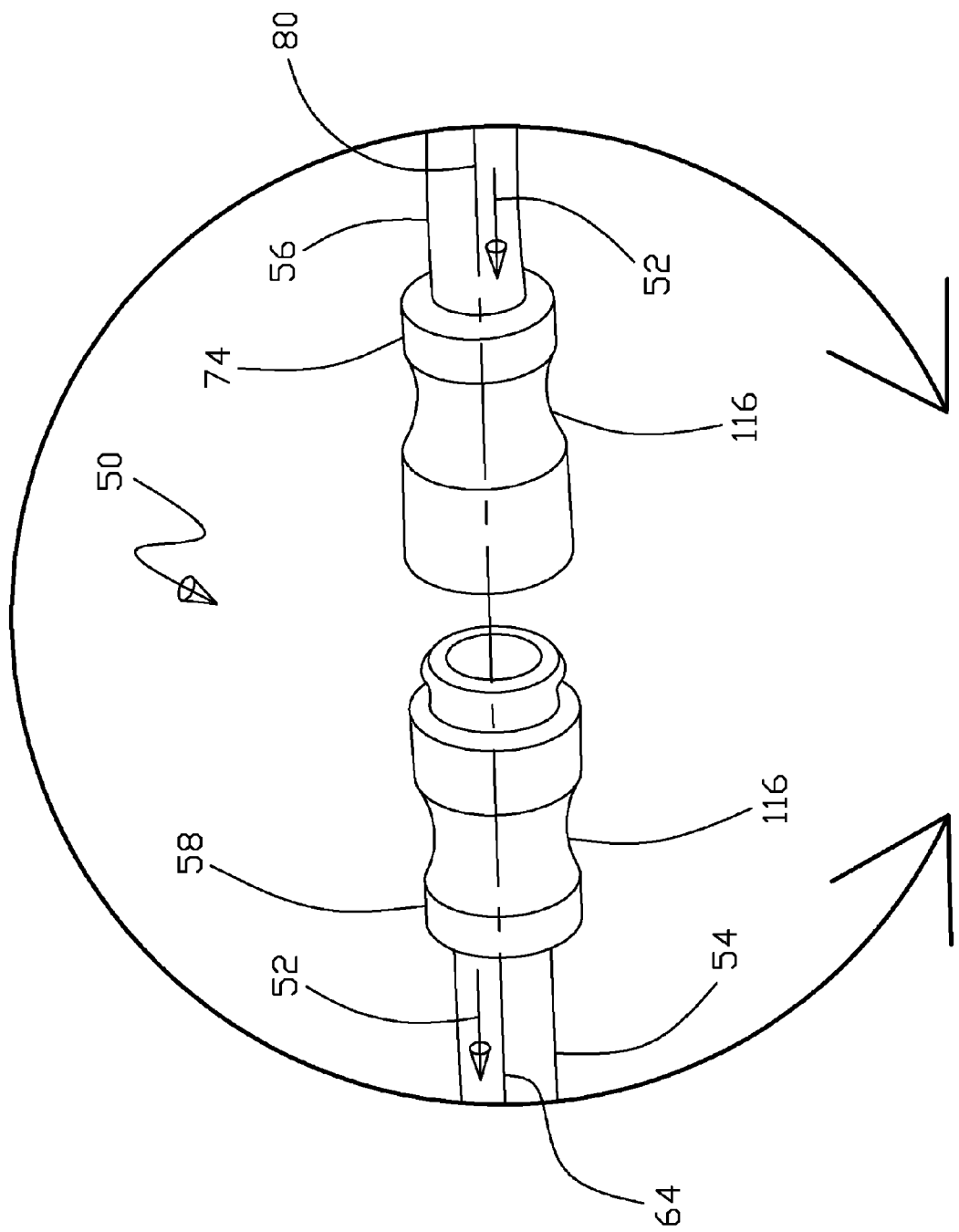
FIG. 28 shows an expanded view close up of the fluid connector in the medical application use as taken from both FIGS. 25 and 26 with the male and female housings removably disengaged from one another.
Figure 29:
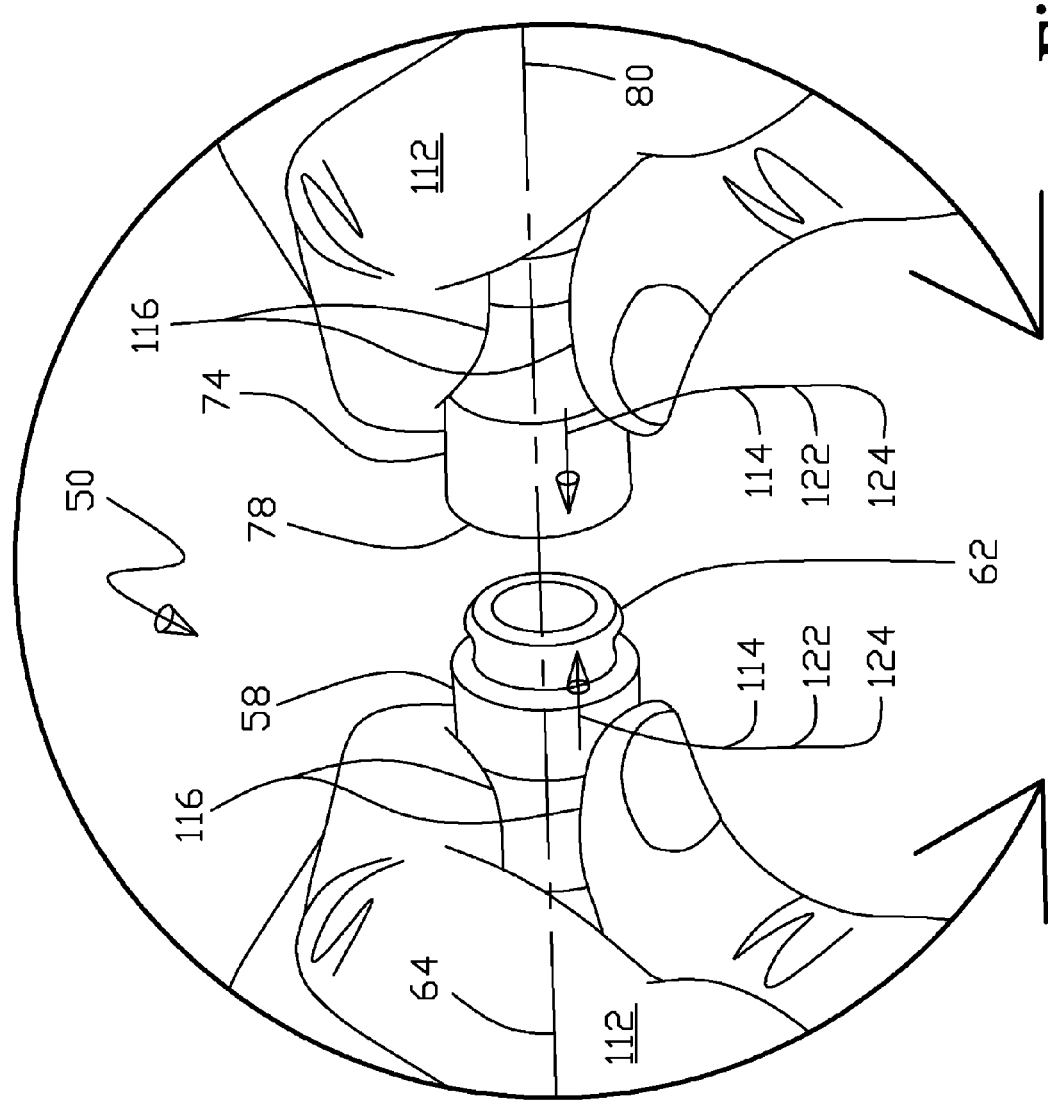
FIG. 29 shows an expanded view close up of the fluid connector in the medical application use as taken from both FIGS. 25 and 26 with the male and female housings removably disengaged from one another to show the manual engaging of the male housing and the female housing that are positioned by the human hand to be substantially co-axial along their respective axes while manually pushing the male and female housing toward one another.

FIG. 25 shows a view of the fluid connector 50 in use in a medical application for delivering oxygen to a human user 111 patient via a first fluid line 54, through the fluid connector 50, and via the second fluid line 56 with fluid communication 52 from an oxygen fluid provider 113 in the medical application. Further, FIG. 26 shows a close up view of the fluid connector 50 in the medical application use as taken from FIG. 25, with the oxygen fluid provider 113 in the medical application delivering oxygen via the first fluid line 54, the fluid connector 50, and the second fluid line 56 with fluid communication 52. Moving onward, FIG. 27 shows an expanded view close up of the fluid connector 50 in the medical application use as taken from both FIGS. 25 and 26 with the male 53 and female 74 housings removably engaged 84 with the fluid communication 52. Next, FIG. 28 shows an expanded view close up of the fluid connector 50 in the medical application use as taken from both FIGS. 25 and 26 with the male 58 and female 74 housings removably disengaged from one another. Further, FIG. 29 shows an expanded view close up of the fluid connector 50 in the medical application use as taken from both FIGS. 25 and 26 with the male 58 and female 74 housings removably disengaged from one another to show the manual engaging 114 and 124 of the male housing 58 and the female housing 74 that are positioned by the human hand 112 to be positioned 122 substantially co-axially along their respective axes 64 and 80 while manually pushing the male 58 and female 74 housing toward one another.

Figure 30:
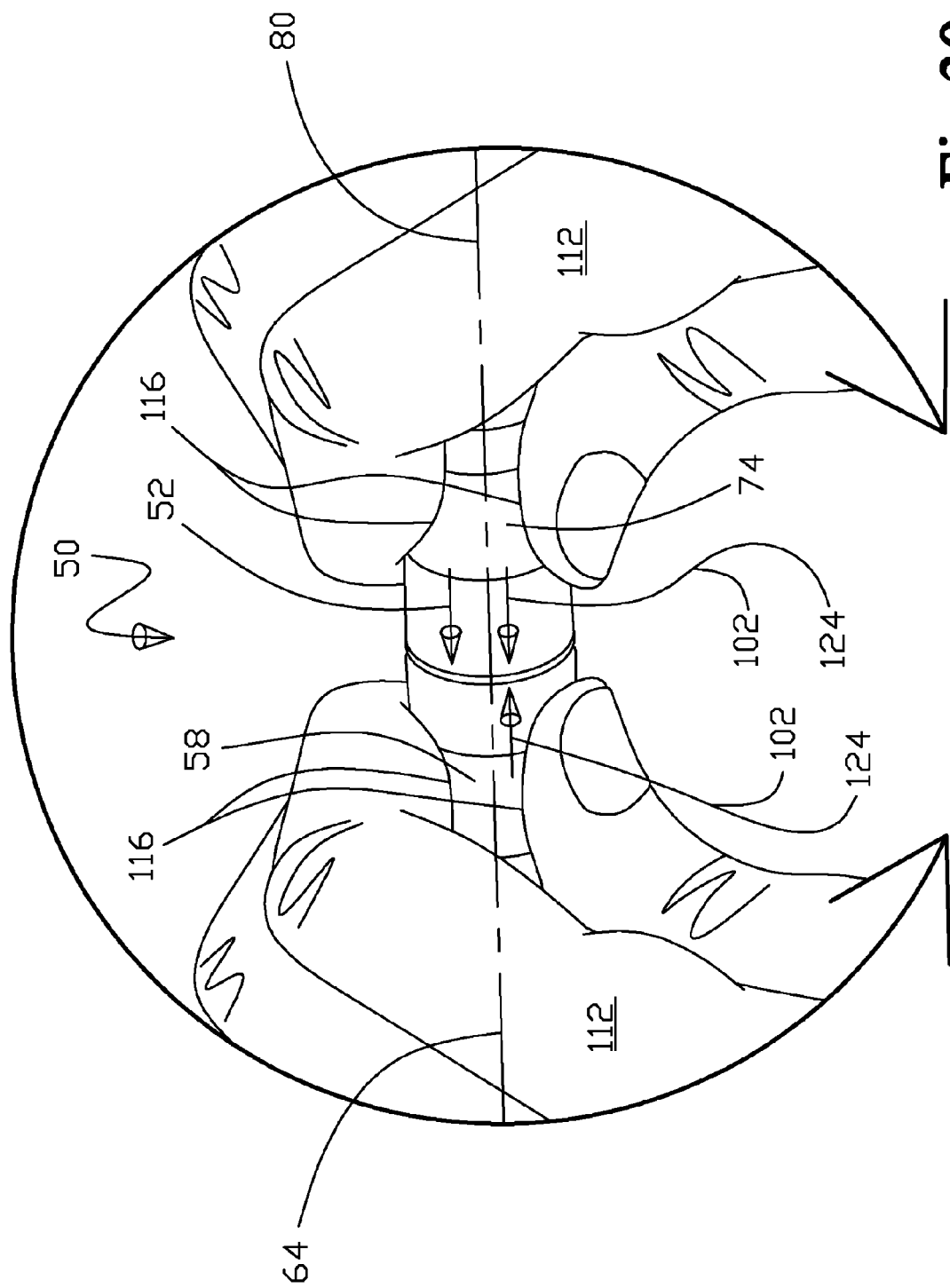
FIG. 30 shows an expanded view close up of the fluid connector in the medical application use as taken from both FIGS. 25 and 26 with the male and female housings removably engaged to one another to show the manual engaging of the male housing and the female housing by manually pushing the male and female housings toward one another to snap them together with only a low axial force being required to allow fluid communication between the first line and the second line.
Figure 31:
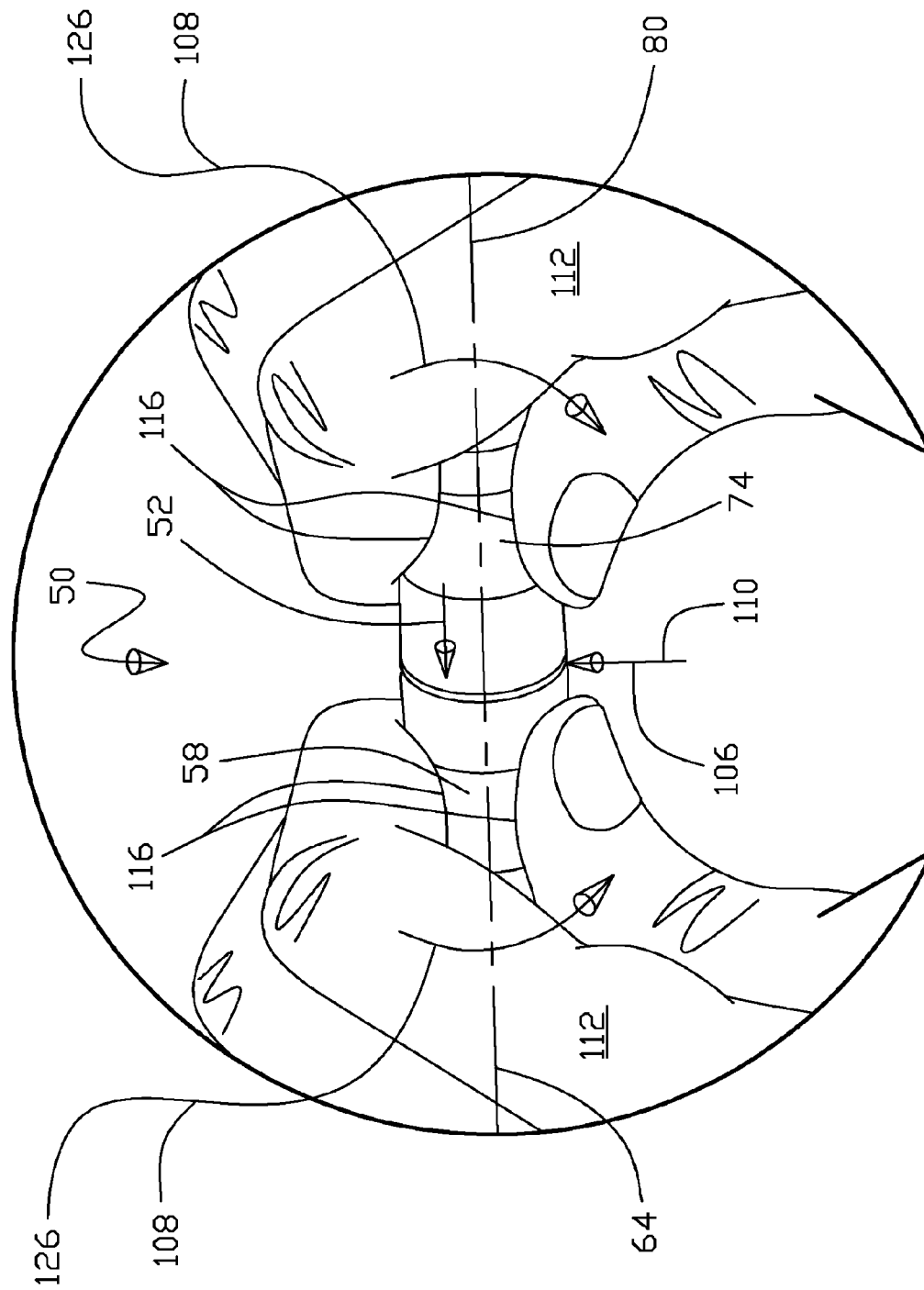
FIG. 31 shows an expanded view close up of the fluid connector in the medical application use as taken from both FIGS. 25 and 26 with the male and female housings removably engaged to one another to show the initial manual disengaging of the male housing and the female housing by manually creating a pushing force between the male and female housings in a direction transverse to the male and female housings longitudinal axes to create a bending moment that will lead to a relatively easy disengagement of the male and female housings as shown in FIG. 32.
Figure 32:
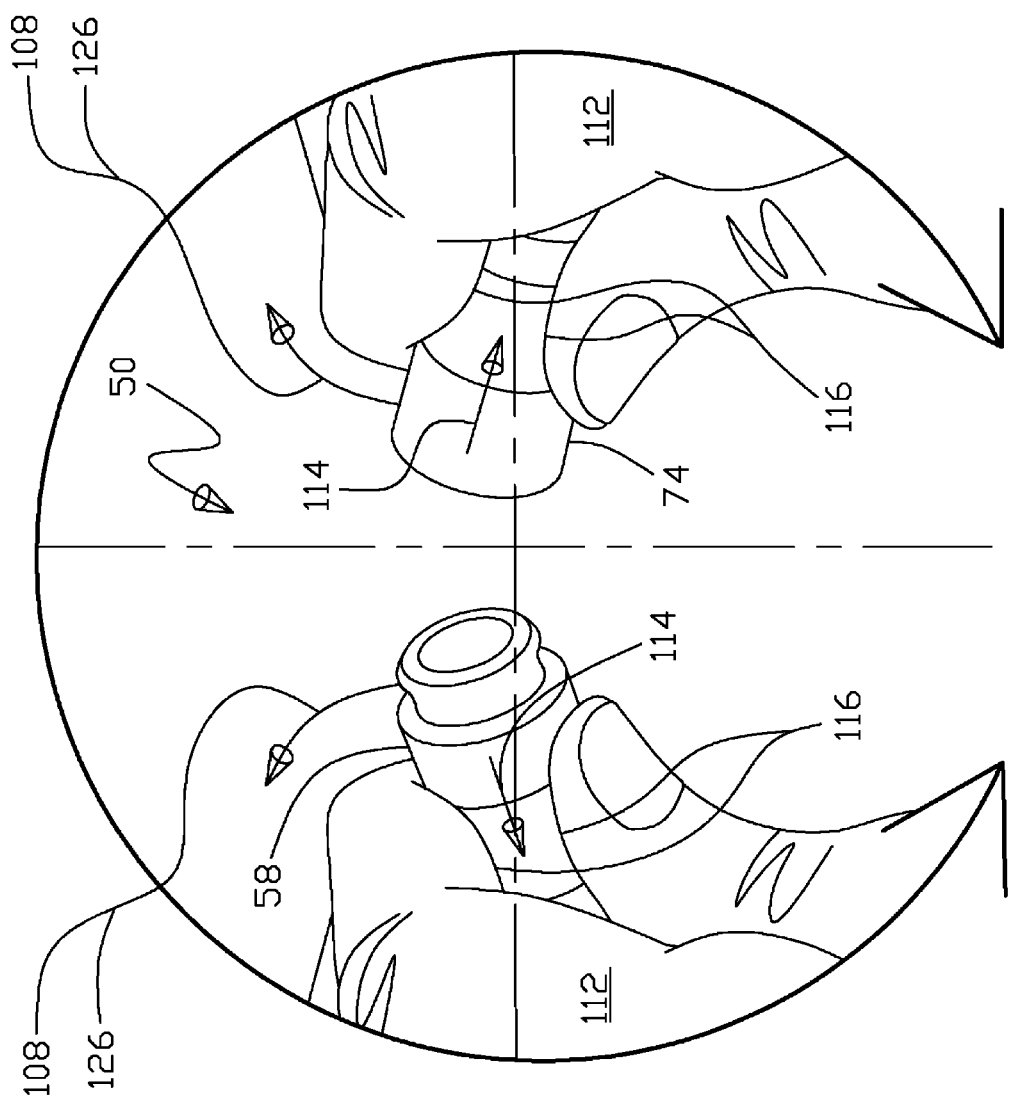
FIG. 32 shows an expanded view close up of the fluid connector in the medical application use as taken from both FIGS. 25 and 26 with the male and female housings removably disengaged from one another as a result of the force between the male and female housings in a direction transverse to the male and female housings longitudinal axes to create the bending moment that results in the relatively easy disengagement of the male and female housings as shown.

Continuing further, FIG. 30 shows an expanded view close up of the fluid connector 50 in the medical application use as taken from both FIGS. 25 and 26 with the male 58 and female 74 housings removably engaged 84 to one another to show the manual engaging of the male 58 housing and the female 74 housing by manually pushing 124 the male 58 and female 74 housings toward one another to snap them together with only a low axial force 102 being required to allow fluid communication 52 between the first fluid line 54 and the second fluid line 56. Moving onward, FIG. 31 shows an expanded view close up of the fluid connector 50 in the medical application use as taken from both FIGS. 25 and 26 with the male 58 and female 74 housings removably engaged 84 to one another to show the initial manual disengaging of the male 58 housing and the female 74 housing by manually creating a pushing force 110 between the male 58 and female 74 housings in a direction transverse 106 to the male 58 and female 74 housings longitudinal axes 64 and 80 respectively to create a bending moment 108 that will lead to a relatively easy disengagement 126 of the male 58 and female 74 housings as shown in FIG. 32. Finally, FIG. 32 shows an expanded view close up of the fluid connector 50 in the medical application use as taken from both FIGS. 25 and 26 with the male 58 and female 74 housings removably disengaged 126 from one another as a result of the force 110 between the male 58 and female 74 housings in a direction transverse 106 to the male 58 and female 74 housings longitudinal axes 64 and 80 respectively to create the bending moment 108 that results in the relatively easy disengagement 114 of the male 58 and female 74 housings as shown.

Broadly the in referring to FIGS. 1 to 24, the present invention of a fluid connector 50 for facilitating fluid communication 52 between a first fluid line 54 and a second fluid line 56 is shown that includes a male housing 58 with a male proximal end portion 60 adapted to be in fluid communication 52 with the first fluid line 54 and a male distal end portion 62 having an elastically deformable ring 66, wherein a male longitudinal axis 64 spans between the male housing proximal end portion 60 and the male housing distal end portion 62. Also broadly included in the fluid connector 50 is a female housing 74 including a female proximal end portion 76 adapted to be in fluid communication 52 with the second fluid line 56 and a female distal end portion 78 with an elastically deformable annulus 82 that removably engages the male housing 58 ring 66, wherein a female longitudinal axis 80 spans between the female housing proximal end portion 76 and the female housing distal end portion 78. Operationally in referring specifically to FIGS. 27 to 32, the male housing 58 and the female housing 74 are sized and configured at the annulus 82 and ring 66 engagement 84 to have a high separating resistance 100 and 104 coaxially substantially along the male 58 and female 74 longitudinal axes 64 and 80 respectively and a low separating resistance 106 substantially transverse 110 to the male 64 and female 80 longitudinal axes by manually applying a bending moment 108 between the male 58 and female 74 engaged housings by application of a manual force 110 substantially transverse to the male 64 and female 80 longitudinal axes during the manual disengaging process 126, as best shown in FIGS. 31 and 32. The preferred materials of construction for the male housing 58 and the female housing 74 is acetal plastic, however, other materials of construction would be acceptable as determined by the application, however requiring some degree of resilience in the selected materials of construction. Further included, is a means 138 for substantially fluid sealing between the male housing 58 and the female housing 74 when the annulus 82 and ring 66 are engaged 84 as best shown in FIGS. 4, 11, and 18.

To further elaborate on the means 138 for substantially fluid sealing, the preferred sealing arrangement is best shown in FIG. 4, and further detailed in FIGS. 5 through 10. This is termed the "face seal" 140 that is further preferably an o-ring 142 as residing in channel 141 and selectively 156 compressed 154 by the tolerance and fit arrangements of the ring 66 and annulus 82, which will be detailed in a later section. The face seal 140 o-ring 142 is positioned adjacent 152 to the annulus 82 and the ring 66. The face seal 140 arrangement shown in FIG. 4 is not a typical prior art face seal in that the o-ring 142 is not contained on three sides within the channel 141, however, with the o-ring 142 only contained within two sides by the channel 141 which simplifies the design and assembly, however, lowering the pressure capability on the o-ring 142 somewhat due to lack of total o-ring 142 containment. Thus the pressure rating is in the range of one hundred (100) pounds per square inch gage (psig) being a moderate pressure rating for the intended applications of the fluid connector 50. The preferred o-ring size is in the range of a one-half (½) inch outside diameter by one-sixteenth (1/16) cross section constructed of Buna-N material. Due to the somewhat smaller size, diameter wise of the preferred o-ring 142 the two sided channel 141 for a face seal 140 application is possible as the internal diameter of the o-ring 142 is not a prone to collapsing inwardly toward the axes 64 and 80, thus allowing the o-ring 142 to be unsupported by the channel 141 on its inner diameter. Note that other sizes and materials for the o-ring 142 are acceptable as being applicable for the desired application. In referring back to FIG. 4, another benefit to the two sided channel 141 design with a face seal 140 o-ring 142 is that it adds axial (along the axes 64 and 80) resilience to the assembly/disassembly to the male 58 and female 74 housings as previously described for FIGS. 27 to 32 as the o-ring 142 is selectively axially compressed 156 by the dimensioning on the annulus 82 and ring 66 removable engagement 84. Also the face seal 140 has the benefit of making the disengagement 126 of the male 58 and female 78 housings easier as best shown in FIG. 32 by allowing the moment 108 movement.

However, for higher sealing pressures than previously described the means 138 for substantial sealing can preferably be a male gland 144 as shown in FIG. 11 for the assembled detail and FIGS. 12 through 17, wherein the o-ring 146 is conventionally retained on three side by the channel 147, with the benefit of the o-ring 146 being fairly well retained by the channel 147 when the male housing 58 and the female housing 74 are not engaged 126, again referring to FIG. 32. The compression of the male gland 144 o-ring 146 is controlled by the channel 147 size and radial fit as between the male 58 and female 74 housings being set by the materials of construction for the male 58 and female 74 housings, the o-ring 146, and the amount of pressure contained by the fluid connector 50. Also as a further sealing alternative for higher pressures that previously described the means 138 for substantial sealing a female gland seal 148 as generally shown assembled in FIG. 18 with detail in FIGS. 19 through 24, again wherein the o-ring 150 is conventionally retained in three sides by the channel 151. Also, the compression of the female gland 148 o-ring 150 is controlled by the channel 151 size and the radial fit between the male housing 58 and the female housing 74, being set by the materials of construction for the male 58 and female 74 housings, the o-ring 150, and the amount of pressure contained by the fluid connector 50. Note that for the means 138 for substantially sealing has been preferably described for o-rings, other types of elastomeric seals would be acceptable such as other cross sections than round and seal types such as packing, "U" cups, segmented seals, and any other seal types that could meet the aforementioned pressures needs and the described applications of the fluid connector 50.

As an option the fluid connector 50 could have the male 58 and female 74 housings being sized and configured 116 to be manually grasped by a human hand 112. As best shown in FIGS. 1 through 3, also FIGS. 4 through 23, and in use in FIGS. 27 through 32. Preferably, an ergometric design is utilized as the previously described Figures show how to facilitate the fluid connector 50 engagement and disengagement 114 in particular in FIGS. 29 through 32. The ergometric design is not limited to what the aforementioned figures show, with the only requirement being to make the human hand 112 grasping of the male 58 and female 74 housings easier. Also to better facilitate the fluid communication 52 and accommodate the previously described means 138 for substantial sealing options the male 58 and female 74 housings could alternatively both or individually be configured with surrounding side walls 65 and 81 respectively that are both substantially about their respective axes 64 and 60, as best shown in FIGS. 4, 11, and 18.

Next focusing upon FIGS. 1 through 3, and specifically the male housing 58 proximal end portion 60 and the female housing 74 proximal end portion 76, can individually or both optionally be as adapted to be in fluid communication 52 with the first fluid line 54 and second fluid line 56 respectively by preferably a barb 132, as shown in FIG. 1, or a thread 134, as shown in FIG. 2, or a luer 136 taper type fitting, as shown in FIG. 3. As the first and second fluid lines 54 and 56 are typically plastic tubing or an acceptable substitute functionally, other adaptations between the housing proximal end portions 60 and 76 and the first and second fluid lines 54 and 56 also respectively would be acceptable that allow sufficient fluid communication 52 as between the fluid lines 54 and 56 and the housings 58 and 74 respectively.

Returning to the annulus 82 and ring 66 removable engagement 84, as best detailed in FIGS. 4, 11, and 18 for the removable engagement 84, and FIGS. 5 through 10, FIGS. 12 through 17, and FIGS. 19 through 24 for detail related to the annulus 82 and ring 66 sizing and configuring radially. The male housing ring 66 has an outside diameter 68 that is sized and configured such that an interference fit of about three (3) percent of the ring outside diameter 68 exists between the ring outside diameter 68 and an inner ridge 88 of the annulus 82. In other words the ring outside diameter 68 is manufactured about three (3) percent larger that the inner ridge 88. The preferred dimensions for the fluid connector 50 being constructed from acetal plastic are for the ring outside diameter 68 to be 0.533±0.001 inches and the inner diameter of the inner ridge 88 to be 0.516±0.001 inches, however, other dimensions and tolerances would be acceptable for different materials, as well as deviations from the aforementioned three (3) percent interference fit for different materials. Wherein, the interference fit is operational to retain the ring 66 within the annulus 82 defining a portion, being radial of the removable engagement 84, however, requiring the materials of construction for the male 58 and female 78 housings to have some degree of resilience.

Further to the annulus 82 and ring 66 removable engagement 84, as best detailed in FIGS. 4, 11, and 18 for the removable engagement 84, and FIGS. 5 through 10, FIGS. 12 through 17, and FIGS. 19 through 24 for detail related to the annulus 82 and ring 66 sizing and configuring axially along axes 64 and 80. The male housing ring outside diameter 68 has an adjacent gradual radius 70 toward the male longitudinal axis 64 opposite of the male proximal end portion 60 and the male housing ring outside diameter 68 also living an opposing adjacent sharp radius 72 toward the male longitudinal radius 64 facing the male proximal end portion 60. Wherein the gradual radius 70, the ring outside diameter 68, and the sharp radius 72 are all disposed within a substantially matching profile of the annulus 82 that is operational to allow a low axial force 102 along the male 64 and female 80 longitudinal axes to engage the ring 66 and the annulus 82 and require a high axial force 100 and 104 along the male 64 and female 80 longitudinal axes to disengage the ring 66 from the annulus 82 along the male longitudinal axis 64, see FIG. 27. This is accomplished by the gradual radius 70 being preferably about 0.054±0.001 inches to ease entry into the inner ridge 88 having a preferred chamfer of about 0.046±0.001 inches axially by about 0.011±0.001 inches radially, being positioned as opposing the female housing proximal end portion 76, thus resulting in the low axial force 102 required for engagement 84 of the annulus 82 and ring 66 as best shown in FIGS. 4, 11, and 18. Conversely, the high axial separating force 100 and 104 as described above is accomplished by the sharp radius 72 that is a chamfer being preferably about 0.019±0.001 inches axially by about 0.012±0.001 inches radially that resides as against the inner ridge 88 chamfer being preferably about 0.034±0.001 axially by about 0.011±0.001 inches radially facing the female housing proximal end portion 76, that results in the aforementioned high axial separating force 100 and 104 by a more blunt interface as between the sharp radius 72 and the inner ridge 88 facing the female housing proximal end portion 76 and compared to the more streamlined interface of the gradual radius 70 and the inner ridge opposite of the female housing proximal end portion 76. Note that other dimensions and tolerances for the gradual radius 10, sharp radius 12 and the inner ridge 88 could be utilized depending upon the materials of construction and the size for the male 58 and female 78 housings.

Further, again to the annulus 82 and ring 66 removable engagement 84, as best detailed in FIGS. 4, 11, and 18 for the removable engagement 84, and FIGS. 5 through 10, FIGS. 12 through 17, and FIGS. 19 through 24 for detail related to the annulus 82 and ring 66 sizing and configuring axially along axes 64 and 80. The fluid connector 50 having the substantially matching profile of the annulus 82 to the gradual radius 70, the ring outside diameter 68, and the sharp radius 72 is modified such that the substantially matching profile has a clearance radial fit and an interference axial fit that is operational to have a substantially tight axial fit between the male housing 58 and the female housing 78 when the annulus 82 and the ring 66 are removably engaged 84. This is accomplished by firstly having a clearance between the ring outside diameter 68 that is preferably about 0.533±0.001 inches and the annulus 82 maximum inside diameter of preferably about 0.538±0.001 inches, thus resulting in a nominal radial clearance of about 0.008 inches. Secondly, by having an interference fit axially (being along the housing longitudinal axes 64 and 80) as the ring 66 having a preferred axial length of about 0.112±0.001 inches and the matching annulus 82 axial length of about 0.098±0.001 inches results in a nominal interference of about 0.014 inches causing a tight axial fit between the male housing 58 and the female housing 78 when they are removably engaged 84, in addition to the tight axial fit setting an axial gage for the axial compression 156 of the face seal 140 o-ring 142 as best shown in FIG. 4. Note that other dimensions and tolerances for the ring outside diameter 68 and ring 66 axial length and annulus 82 maximum inside diameter and axial length could be utilized depending upon the materials of construction and the size for the male 58 and female 78 housings for adjustment of the axial fit and face seal 140 o-ring 142 compression.

Method of Use

Referring primarily to FIGS. 25 through 32 a method of using the fluid connector 50 is given for manually engaging 102 and manually disengaging 126 the fluid communication 52 between the first fluid line 54 and the second fluid line 56, comprising the following steps. Firstly providing a fluid connector 50 that includes a male housing 58 with a male proximal end portion 60 adapted to be in fluid communication 52 with the first fluid line 54 and a male distal end portion 62 having an elastically deformable ring 66. Wherein a male longitudinal axis 64 spans between the male housing proximal end portion 60 and the male housing distal end portion 62. Also provided is a female housing 74 having a female proximal end portion 76 adapted to be in fluid communication 52 with the second fluid line 56 and a female distal end portion 78 with an elastically deformable annulus 82 that removably engages the ring 66. Wherein a female longitudinal axis 80 spans between the female housing proximal end portion 76 and the female housing distal end portion 78. Operationally the male housing 58 and the female housing 78 are sized and configured at the annulus 82 and ring 66 engagement 84 to have a high separating resistance 100 coaxially substantially along the male 64 and female 80 longitudinal axes and a low separating resistance 106 substantially transverse to the male 64 and female 80 longitudinal axes by manually applying a bending moment 108 between the male 58 and female 74 engaged housings by application of a manual force 106 substantially transverse to the male 64 and female 80 longitudinal axes. Also provided is a means 138 for substantially fluid sealing between the male housing 58 and the female housing 74 when the annulus 82 and ring 66 are engaged 84.

Secondly a step of attaching the male proximal end portion 60 to the first fluid line 54 and thirdly a step of attaching the female proximal end portion 76 to the second fluid line 56 as best shown in FIG. 28 and in looking at FIGS. 1, 2, and 3 for the options of the attachment adaptation of the proximal end portion 60 and 76 to the fluid lines 54 and 56 via a barb 132, thread 134, or luer taper 136, or other types of fluid line connections. Continuing, to a fourth step of positioning 122 manually the male housing longitudinal axis 64 and the female longitudinal axis 80 to be substantially co-axial with the male housing distal end 62 and the female housing distal end 78 facing one another as best shown in FIGS. 28 and 29. Next, a fifth step of pushing 124 the male housing distal end 62 and the female housing distal end 78 together manually with a low required engagement axial force 102 such that the ring 66 causes an engagement 84 with the annulus 82, facilitating the substantially sealed fluid communication 52 between the first fluid line 54 and the second fluid line 56 with having a high engagement retaining force 104 between the male 58 and female 74 housings substantially along the male housing longitudinal axis 64 and the female housing longitudinal axis 80 as best shown in FIGS. 29 and 30. Further, a sixth step of creating a bending moment 108 at the ring 66 and annulus 82 engagement 84 by applying a tow force 110 substantially transverse 106 to the male housing longitudinal axis 64 and the female housing longitudinal axis 80, operationally causing disengagement 126 of the ring 66 and annulus 82 and therefore the male 58 and female 74 housings as best shown in FIGS. 31 and 32. Thus the fluid connector 50 separates into the male 58 and female 74 housings relatively easily by application of the transverse force 106 and 110 as the separating force 126 applies to only a portion of the engagement 84 circumference resulting in an easier disengagement as opposed to the higher disengagement force 100 required when the housings 58 and 74 are pulled apart along the axes 64 and 80 wherein all of the engagement 84 circumference is engaged.

CONCLUSION

Accordingly, the present invention of a fluid connector 50 has been described with some degree of particularity directed to the embodiments of the present invention. It should be appreciated, though, that the present invention is defined by the following claims construed in light of the prior art so modifications the changes maybe made to the exemplary embodiments of the present invention without departing from the inventive concepts contained therein.

The invention claimed is:

1. A fluid connector for facilitating fluid communication between a first line and a second line, comprising:

(a) a male housing including a male proximal end portion adapted to be in fluid communication with the first line and a male distal end portion, wherein a male longitudinal axis spans between said male housing proximal end portion and said male housing distal end portion, said male housing distal end portion, having an elastically deformable ring, said ring having an outside diameter, also a gradual radius that is adjacent to said outside diameter and adjacent to said distal end portion, a sharp radius that is adjacent to said outside diameter facing said male proximal end portion, and an axial fit interference interface that is positioned axially between said sharp radius and said male proximal end portion, wherein said axial fit interference interface is perpendicular to said male longitudinal axis;

(b) a female housing including a female proximal end portion adapted to be in fluid communication with the second line and a female distal end portion, wherein a female longitudinal axis spans between said female housing proximal end portion and said female housing distal end portion, said female housing distal end portion having an elastically deformable annulus that includes an inner ridge adjacent to said annulus on said distal end portion, and an axial fit interference interface that is positioned axially at a termination of said female housing distal end portion, wherein said axial fit interference interface is perpendicular to said female longitudinal axis, wherein said male housing ring outside diameter having an interference fit with said inner ridge and said male housing ring outside diameter having a clearance fit with said annulus, further said gradual radius enters said inner ridge with a lower axial force required for engagement of said annulus and said ring along said female and male longitudinal axes, wherein once said male and said female housings are engaged when said male and female housing axial fit interference interfaces are in bearing contact preventing axial movement as between said male and female housings, said clearance results in a higher axial separating force as said sharp radius and said inner ridge having a more blunt interface then said gradual radius and said inner ridge to require more force to disengage said female and male housing than to engage said female and male housing along said female and male longitudinal axes, wherein said gradual radius, said male housing ring outside diameter, and said sharp radius are all disposed within a substantially matching profile of said annulus to said gradual radius, wherein operationally said male housing and said female housing are sized and configured at said annulus and ring engagement to have a high separating resistance coaxially substantially along said female and male longitudinal axes and a low separating resistance substantially transverse to said male and female longitudinal axes by manually applying a bending moment between said male and female engaged housings by application of a manual force substantially transverse to said male and female longitudinal axes at an axial fit between said male and female housings, said force applies to only a portion of an engagement circumference as between said male and female housings due to said axial fit, resulting in easier disengagement of said male and female housings; and (c) a means for substantially fluid sealing between said male housing and said female housing when said annulus and ring are engaged.

2. A fluid connector according to claim 1 wherein said male and female housings are sized and configured to be manually grasped by a human hand.

3. A fluid connector according to claim 1 wherein said male housing is constructed of a male surrounding sidewall that is substantially about said male housing longitudinal axis.

4. A fluid connector according to claim 1 wherein said female housing is constructed of a female surrounding sidewall that is substantially about said female housing longitudinal axis.

5. A fluid connector according to claim 1 wherein said male housing proximal end portion being adapted to be in fluid communication with the first line is selected from the group consisting essentially of barbs, threads, and a luer taper.

6. A fluid connector according to claim 1 wherein said female housing proximal end portion being adapted to be in fluid communication with the second line is selected from the group consisting essentially of barbs, threads, and a luer taper.

7. A fluid connector according to claim 1 wherein said male and female housings are constructed of an acetal plastic.

8. A fluid connector according to claim 7 wherein said male housing ring has an outside diameter that is sized and configured such that an interference fit of about three (3) percent of said ring outside diameter exists between said ring outside diameter and an inner ridge of said annulus, wherein said interference fit is operational to retain said ring within said annulus defining a portion of said removable engagement.

9. A fluid connector according to claim 8 wherein said substantially matching profile of said annulus to said gradual radius, said ring outside diameter, and said sharp radius is modified such that said substantially matching profile has a clearance radial fit of about one and a half (1.5) percent of said ring outside diameter and an interference axial fit of about one and a half (1.5) percent of an annulus axial length that is operational to have a substantially tight axial fit between said male housing and said female housing.

10. A fluid connector according to claim 1 wherein said means for substantially fluid sealing between said male housing and said female housing is a face seal.

11. A fluid connector according to claim 10 wherein said face seal is an o-ring.

12. A fluid connector for facilitating fluid communication between a first line and a second line, comprising:

(a) a male housing including a male proximal end portion adapted to be in fluid communication with the first line and a male distal end portion, wherein a male longitudinal axis spans between said male housing proximal end portion and said male housing distal end portion, said male housing distal end portion, having an elastically deformable ring, said ring having an outside diameter, also a gradual radius that is adjacent to said outside diameter and adjacent to said distal end portion, a sharp radius that is adjacent to said outside diameter facing said proximal end, and an axial fit interference interface that is positioned axially between said sharp radius and said proximal end, wherein said axial fit interference interface is perpendicular to said male longitudinal axis;

(b) a female housing including a female proximal end portion adapted to be in fluid communication with the second line and a female distal end portion, wherein a female longitudinal axis spans between said female housing proximal end portion and said female housing distal end portion, said female housing distal end portion having an elastically deformable annulus that includes an inner ridge adjacent to said annulus on said distal end portion, and an axial fit interference interface that is positioned axially at a termination of said female housing distal end portion, wherein said axial fit interference interface is perpendicular to said female longitudinal axis wherein said male housing ring outside diameter having an interference fit with said inner ridge and said male housing ring outside diameter having a clearance fit with said annulus, further said gradual radius enters said inner ridge with a lower axial force required for engagement of said annulus and said ring along said female and male longitudinal axes, wherein once said male and said female housings are engaged when said male and female housing axial fit interference interfaces are in bearing contact preventing axial movement as between said male and female housings, said clearance results in a higher axial separating force as said sharp radius and said inner ridge having a more blunt interface then said gradual radius and said inner ridge to require more force to disengage said female and male housing than to engage said female and male housing along said female and male longitudinal axes, wherein operationally said male housing and said female housing are sized and configured at said annulus and ring engagement to have a high separating resistance coaxially substantially along said female and male longitudinal axes and a low separating resistance substantially transverse to said male and female longitudinal axes by manually applying a bending moment between said male and female engaged housings by application of a manual force substantially transverse to said male and female longitudinal axes at an axial fit between said male and female housings, said force applies to only a portion of an engagement circumference as between said male and female housings due to said axial fit, resulting in easier disengagement of said male and female housings; and (c) a face seal for substantially fluid sealing between said male housing and said female housing when said annulus and ring are engaged, wherein said face seal resides in a partially contained seal channel, wherein axial compression of said seal is controlled by said male and said female housings being engaged when said male and female housing axial fit interference interfaces are in bearing contact, with at least a portion of said seal completely unsupported by said seal channel when said male and female housings are assembled.

13. A fluid connector according to claim 12 wherein said face seal is an o-ring that is contained on three sides, with one side not contained having direct line of sight exposure to the fluid communication.

14. A fluid connector according to claim 13 wherein said o-ring is selectively compressed axially substantially along said male and female longitudinal axes between said male and female housings by a selected fit between said ring and said annulus when engaged to act as an axial gage for substantially controlling said selected o-ring compression.

15. A method of using a fluid connector for manually engaging and manually disengaging a fluid communication between a first line and a second line, comprising the steps of:

(a) providing a fluid connector that includes a male housing including a male proximal end portion adapted to be in fluid communication with the first line and a male distal end portion, wherein a male longitudinal axis spans between said male housing proximal end portion and said male housing distal end portion, said male housing distal end portion, having an elastically deformable ring, said ring having an outside diameter, also a gradual radius that is adjacent to said outside diameter and adjacent to said distal end portion, a sharp radius that is adjacent to said outside diameter facing said male proximal end portion, and an axial fit interference interface that is positioned axially between said sharp radius and said male proximal end portion, wherein said axial fit interference interface is perpendicular to said male longitudinal axis, in addition a female housing including a female proximal end portion adapted to be in fluid communication with the second line and a female distal end portion, wherein a female longitudinal axis spans between said female housing proximal end portion and said female housing distal end portion, said female housing distal end portion having an elastically deformable annulus that includes an inner ridge adjacent to said annulus on said female housing distal end portion, and an axial fit interference interface that is positioned axially at a termination of said female housing distal end portion, wherein said axial fit interference interface is perpendicular to said female longitudinal axis, wherein said male housing ring outside diameter having an interference fit with said inner ridge and said male housing ring outside diameter having a clearance fit with said annulus, further said gradual radius enters said inner ridge with a lower axial force required for engagement of said annulus and said ring along said female and male longitudinal axes, wherein once said male and said female housings are engaged when said male and female housing axial fit interference interfaces are in bearing contact preventing axial movement as between said male and female housings, said clearance results in a higher axial separating force as said sharp radius and said inner ridge having a more blunt interface then said gradual radius and said inner ridge to require more force to disengage said female and male housing than to engage said female and male housing along said female and male longitudinal axes, wherein operationally said male housing and said female housing are sized and configured at said annulus and ring engagement to have a high separating resistance coaxially substantially along said female and male longitudinal axes and a low separating resistance substantially transverse to said male and female longitudinal axes by manually applying a bending moment between said male and female engaged housings by application of a manual force substantially transverse to said male and female longitudinal axes at an axial fit between said male and female housings, said force applies to only a portion of an engagement circumference as between said male and female housings due to said axial fit creating a bearing force at a portion of said axial fit, resulting in a diametrically opposed separating force at said sharp radius and said inner ridge interference resulting in an easier disengagement of said male and female housings;

(b) attaching said male proximal end portion to the first line;

(c) attaching said female proximal end portion to the second line;

(d) positioning said male housing longitudinal axis and said female longitudinal axis to be substantially co-axial with said male housing distal end and said female housing distal end facing one another;

(e) pushing said male housing distal end and said female housing distal end together manually such that said ring causes an engagement with said annulus, wherein once said male and said female housings are engaged when said male and female housing axial fit interference interfaces are in bearing contact preventing axial movement as between said male and female housings, facilitating substantially sealed fluid communication between the first line and the second line with having a high engagement force between said male and female housings substantially along said male housing longitudinal axis and said female housing longitudinal axis; and (f) creating a bending moment at said ring and annulus engagement by applying a low force substantially transverse to said male housing longitudinal axis and said female housing longitudinal axis, wherein said applied force for separating will be focused on a small area of said annulus, opposite said applied force, operationally causing disengagement of said ring and annulus and therefore said male and female housings, wherein said force is applied at an axial fit interface between said male and female housings, said force applies to only a portion of an engagement circumference as between said male and female housings due to said axial fit creating a bearing force at a portion of said axial fit, resulting in a diametrically opposed separating force at said sharp radius and said inner ridge interference resulting in an easier disengagement of said male and female housings.

* * * * *